(12) United States Patent
Bohana-Kashtan et al.

(10) Patent No.: US 11,066,642 B2
(45) Date of Patent: *Jul. 20, 2021

(54) PREPARATION OF RETINAL PIGMENT EPITHELIUM CELLS

(71) Applicant: CELL CURE NEUROSCIENCES LTD, Jerusalem (IL)

(72) Inventors: Osnat Bohana-Kashtan, Tel-Mond (IL); Ofer Wiser, Jerusalem (IL)

(73) Assignee: Cell Cure Neurosciences LTD, Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/750,108

(22) PCT Filed: Aug. 4, 2016

(86) PCT No.: PCT/IL2016/050857
§ 371 (c)(1),
(2) Date: Feb. 2, 2018

(87) PCT Pub. No.: WO2017/021973
PCT Pub. Date: Feb. 9, 2017

(65) Prior Publication Data
US 2018/0230426 A1 Aug. 16, 2018

Related U.S. Application Data

(60) Provisional application No. 62/201,156, filed on Aug. 5, 2015, provisional application No. 62/253,738, filed on Nov. 11, 2015.

(51) Int. Cl.
*C12N 5/079* (2010.01)

(52) U.S. Cl.
CPC ........ *C12N 5/0621* (2013.01); *C12N 2500/38* (2013.01); *C12N 2500/98* (2013.01); *C12N 2501/115* (2013.01); *C12N 2501/15* (2013.01); *C12N 2506/02* (2013.01); *C12N 2533/52* (2013.01); *C12N 2533/54* (2013.01)

(58) Field of Classification Search
CPC .......... C12N 5/0621; C12N 2501/15
See application file for complete search history.

(56) References Cited

U.S. PATENT DOCUMENTS

| | | | |
|---|---|---|---|
| 3,791,932 A | 2/1974 | Schuurs et al. | |
| 3,839,153 A | 10/1974 | Schuurs et al. | |
| 3,850,578 A | 11/1974 | McConnell | |
| 3,850,752 A | 11/1974 | Schuurs et al. | |
| 3,853,987 A | 12/1974 | Dreyer | |
| 3,867,517 A | 2/1975 | Ling | |
| 3,879,262 A | 4/1975 | Schuurs et al. | |
| 3,901,654 A | 8/1975 | Gross | |
| 3,935,074 A | 1/1976 | Rubenstein et al. | |
| 3,984,533 A | 10/1976 | Uzgiris | |
| 3,996,345 A | 12/1976 | Ullman et al. | |
| 4,034,074 A | 7/1977 | Miles | |
| 4,098,876 A | 7/1978 | Piasio et al. | |
| 4,666,828 A | 5/1987 | Gusella | |
| 4,683,202 A | 7/1987 | Mullis | |
| 4,801,531 A | 1/1989 | Frossard | |
| 4,879,219 A | 11/1989 | Wands et al. | |
| 5,011,771 A | 4/1991 | Bellet et al. | |
| 5,192,659 A | 3/1993 | Simons | |
| 5,272,057 A | 12/1993 | Smulson et al. | |
| 5,281,521 A | 1/1994 | Trojanowski et al. | |
| 5,755,785 A | 5/1998 | Rowsey et al. | |
| 5,843,780 A | 12/1998 | Thomson | |
| 5,941,250 A | 8/1999 | Aramant et al. | |
| 5,962,027 A | 10/1999 | Hughes | |
| 6,045,791 A | 4/2000 | Liu | |
| 6,090,622 A | 7/2000 | Gearhart et al. | |
| 7,267,981 B2 | 9/2007 | Amit et al. | |
| 8,956,866 B2 | 2/2015 | Idelson et al. | |
| 2009/0196860 A1 | 8/2009 | Amit et al. | |
| 2013/0196369 A1 | 8/2013 | Hikita et al. | |
| 2015/0010922 A1 | 1/2015 | Reubinoff et al. | |

FOREIGN PATENT DOCUMENTS

| | | | | |
|---|---|---|---|---|
| CN | 101688178 A | 3/2010 | | |
| CN | 103555654 A | 2/2014 | | |
| CN | 104136034 A | 11/2014 | | |
| EP | 2 128 244 A1 | 12/2009 | | |
| EP | 2383333 A1 | * 11/2011 | ........... | C12N 5/0621 |
| GB | 2 327 675 A | 2/1999 | | |
| JP | 2010524457 A | 7/2010 | | |
| WO | WO-01/55114 A1 | 8/2001 | | |
| WO | WO-02/060875 A1 | 8/2002 | | |
| WO | WO-03/068233 A1 | 8/2003 | | |
| WO | WO-2005/014549 A1 | 2/2005 | | |

(Continued)

OTHER PUBLICATIONS

Buchholz et al. "Rapid and Efficient Directed Differentiation of Human Pluripotent Stem Cells Into Retinal Pigmented Epithelium" Stem Cells Translationalmedicine 2013;2:384-393 (Year: 2013).*
Liu et al. "Chemical Modulation of Cell Fate in Stem Cell Therapeutics and Regenerative Medicine", Cell Chemical Biology Aug. 18, 2016, 24 pages (Year: 2016).*
Jang et al. "Modulation of Stem Cell Differentiation with Biomaterials" International Journal of Stem Cells vol. 3, No. 2, 2010, 5 pgs (Year: 2010).*
Strassburg et al. "Co-culture induces mesenchymal stem cell differentiation and modulation of the degenerate human nucleus pulposus cell phenotype" Regen. Med. (2010) 5(5), 701-711 (Year: 2010).*
Mekala et al. "Derivation, characterization and retinal differentiation of induced pluripotent stem cells" J. Biosci. 38(1), Mar. 2013, 123-134 (Year: 2013).*

(Continued)

*Primary Examiner* — Thane Underdahl
(74) *Attorney, Agent, or Firm* — Mintz, Levin, Cohn, Ferris, Glovsky and Popeo, P.C.

(57) ABSTRACT

A method of generating retinal pigment epithelium cells is disclosed. Cell populations comprising same and uses thereof are also disclosed.

20 Claims, 13 Drawing Sheets

(56) References Cited

FOREIGN PATENT DOCUMENTS

| | | | |
|---|---|---|---|
| WO | WO-2006/070370 A2 | 7/2006 | |
| WO | WO-2008/129554 A1 | 10/2008 | |
| WO | WO-2013/114360 A1 | 8/2013 | |
| WO | WO-2013/114360 A8 | 9/2013 | |
| WO | WO-2013/184809 A1 | 12/2013 | |
| WO | WO-2014/121077 A2 | 8/2014 | |
| WO | WO-2015/087231 A1 | 6/2015 | |
| WO | WO-2016/108239 A1 | 7/2016 | |
| WO | WO-2016/108240 A1 | 7/2016 | |
| WO | WO-2017/017686 A1 | 2/2017 | |

OTHER PUBLICATIONS

Idelson et al. "Directed Differentiation of Human Embryonic Stem Cells into Functional Retinal Pigment Epithelium Cells" Cell Stem Cell 5, 396-408, Oct. 2, 2009 (Year: 2009).*

Kosovsky et al. "3D Cell CultureSystems" Feb. 16, 2011, 48 pgs (Year: 2011).*

Singh et al. "Functional Analysis of Serially Expanded Human iPS Cell-Derived RPE Cultures" Invest Ophthalmol Vis Sci. 2013;54:6767-6778 (Year: 2013).*

Gamm et al. "A Novel Serum-Free Method for Culturing Human Prenatal Retinal Pigment Epithelial Cells" Invest Ophthalmol Vis Sci . 2008;49:788-799 (Year: 2008).*

International Search Report and Written Opinion issued in International Application No. PCT/IL2016/050857, dated Dec. 10, 2016 (Oct. 12, 2016) 11 pages.

Lane, A. et al. (2014, e-published in SCTM *Express* Oct. 1, 2014). "Engineering Efficient Retinal Pigment Epithelium Differentiation From Human Pluripotent Stem Cells." *Stem Cells Translational Medicine:SCTM*, 3(11):1295-1304.

International Preliminary Report on Patentability issued in International Application No. PCT/IL2016/050857, dated Feb. 15, 2018, 9 pages.

Bharti et al. (Feb. 7, 2011) "The New Paradigm: Retinal Pigment Epithelium Cells Generated From Embryonic or Induced Pluripotent Stem Cells", Pigment Cell & Melanoma Research, 24(1):21-34 (21 pages).

Peng et al. (Feb. 2014) "Differentiation of Human Umbilical Cord Mesenchymal Stem Cells into Retinal Pigment Epithelial Like Cells", Chinese Journal of Cells and Stem Cells, 4(1):44-51. (English Abstract Submitted).

* cited by examiner

PREPARATION OF RETINAL PIGMENT EPITHELIUM CELLS

CROSS-REFERENCE TO RELATED APPLICATIONS

This application is a National Phase Application of PCT/IL2016/050857, filed Aug. 4, 2016, which claims benefit under 35 USC § 119(e) to U.S. Provisional Application No. 62/201,156, filed Aug. 5, 2015, and U.S. Provisional Application No. 62/253,738, filed Nov. 11, 2015, which are incorporated herein by reference in their entirety.

FIELD AND BACKGROUND OF THE INVENTION

The present invention, in some embodiments thereof, relates to methods of preparing retinal pigment epithelium cells from pluripotent stem cells.

The present invention, in some embodiments thereof, relates to retinal pigment epithelium cells and, more particularly, but not exclusively, to assessment of such cells as a therapeutic. The present invention also relates to generation of retinal pigment epithelium cells from embryonic stem cells.

The retinal pigmented epithelium (RPE) is a monolayer of pigmented cells, which lies between the neural retina and the choriocapillaris. The RPE cells play crucial roles in the maintenance and function of the retina and its photoreceptors. These include the formation of the blood-retinal barrier, absorption of stray light, supply of nutrients to the neural retina, regeneration of visual pigment, and uptake and recycling of shed outer segments of photoreceptors.

Retinal tissue may degenerate for a number of reasons. Among them are: artery or vein occlusion, diabetic retinopathy and retinopathy of prematurity, which are usually non-hereditary. There are hereditary diseases such as retinitis pigmentosa, retinoschisis, lattice degeneration, Best disease, Stargardt disease which also involve retinal tissue degeneration. A common retinal degeneration condition is age related macular degeneration (AMD). These conditions are characterized by progressive types of retinal degeneration.

RPE cells may potentially be used for cell replacement therapy of the degenerating RPE in retinal diseases mentioned above. They may be also used as a vehicle for the introduction of genes for the treatment of retinal degeneration diseases. In addition, these cells can be used in combination with other cells (such as photoreceptors) or in combination with small molecules. These cells may also serve as an in vitro model of retinal degeneration diseases, as a tool for high throughput screening for a therapeutic effect of small molecules, and for the discovery and testing of new drugs for retinal degeneration diseases. RPE cells could also be used for basic research of RPE development, maturation, characteristics, properties, metabolism, immunogenicity, function and interaction with other cell types.

Human fetal and adult RPE has been used as an alternative donor source for allogeneic transplantation. However, practical problems in obtaining sufficient tissue supply and the ethical concerns regarding the use of tissues from aborted fetuses limit widespread use of these donor sources. Given these limitations in supply of adult and fetal RPE grafts, the potential of alternative donor sources have been studied. Human pluripotent stem cells provide significant advantages as a source of RPE cells for transplantation. Their pluripotent developmental potential may enable their differentiation into authentic functional RPE cells, and given their potential for infinite self renewal, they may serve as an unlimited donor source of RPE cells. Indeed, it has been demonstrated that human embryonic stem cells (hESCs) and human induced pluripotent stem cells (iPSCs) may differentiate into RPE cells in vitro, attenuate retinal degeneration and preserve visual function after subretinal transplantation to the Royal College of Surgeons (RCS) rat model of retinal degeneration that is caused by RPE dysfunction. Therefore, pluripotent stem cells may be an unlimited source for the production of RPE cells.

Current protocols for the derivation of RPE cells from pluripotent stem cells are labor intensive and time-consuming, yielding limited numbers of pigmented cells. New methods are required to produce RPE cells in quantities large enough that they can be used in the clinical setting.

Background art includes WO 2013/114360, WO 2008/129554 and WO 2013/184809.

SUMMARY OF THE INVENTION

According to an aspect of some embodiments of the present invention there is provided a method of generating retinal pigment epithelial (RPE) cells comprising:

(a) culturing a population of human pluripotent stem cells in a medium comprising a differentiating agent to obtain differentiating cells;

(b) culturing the differentiating cells in a culture comprising a medium which comprises one or more members of the TGFβ superfamily, thereby generating a mixed population of cells comprising RPE cells;

(c) removing the mixed population of cells from the culture, wherein more than 10% of the cells of the mixed population of cells are non-pigmented cells; and subsequently;

(d) culturing the mixed population of cells on an adherent surface to generate an expanded population of RPE cells; and (e) harvesting the expanded population of RPE cells, thereby generating the RPE cells.

According to an aspect of some embodiments of the present invention there is provided a population of RPE cells generated according to the method described herein.

According to an aspect of some embodiments of the present invention there is provided a method of treating a retinal or neurodegenerative disease or disorder in a subject in need thereof comprising administering a therapeutically effective amount of the RPE cells described herein to the subject thereby treating the retinal or neurodegenerative disease or disorder.

According to an aspect of some embodiments of the present invention, there is provided a method of treating a retinal or neurodegenerative disease or disorder in a subject in need thereof comprising:

(a) generating RPE cells according to the method described herein; and (b) transplanting a therapeutically effective amount of the RPE cells into the subject's eye following the harvesting, thereby treating the disease.

According to some embodiments of the invention, step (c) is effected enzymatically.

According to some embodiments of the invention, more than 50% of all the cells in the culture are removed in step (c).

According to some embodiments of the invention, the method further comprises expanding the human pluripotent stem cells prior to step (a).

According to some embodiments of the invention, more than 70% of the cells of the expanded population of RPE cells are CRALBP⁺PMEL17⁺.

According to some embodiments of the invention, the adherent surface is selected from the group consisting of gelatin, fibronectin, laminin, collagen I and collagen IV.

According to some embodiments of the invention, the culturing of the population of cells on the adherent surface is effected for at least 3 weeks.

According to some embodiments of the invention, the culturing of the population of cells on the adherent surface is effected for at least 8 passages.

According to some embodiments of the invention, the method further comprises cryopreserving the RPE cells following step (e).

According to some embodiments of the invention, the cryopreserving is effected in a medium selected from the group consisting of 90% Human Serum/10% DMSO, CryoStor 2%, CryoStor 5% and CryoStor 10%, and Stem Cell Banker.

According to some embodiments of the invention, the human pluripotent stem cells comprise human embryonic stem cells.

According to some embodiments of the invention, the differentiating agent comprises nicotinamide.

According to some embodiments of the invention, the medium of step (a) is devoid of activin A.

According to some embodiments of the invention, the member of the TGFβ superfamily is selected from the group consisting of TGFβ1, TGFβ3 and activin A.

According to some embodiments of the invention, the medium of step (b) comprises nicotinamide and activin A.

According to some embodiments of the invention, the expanded population of RPE cells has undergone more than 30 cell doublings.

According to some embodiments of the invention, the method further comprises a step of culturing the RPE cells in a medium comprising nicotinamide and devoid of activin A following step (b) and prior to step (c).

According to some embodiments of the invention, step (a) is effected under non-adherent conditions.

According to some embodiments of the invention, step (a) is effected initially under non-adherent conditions and subsequently under adherent conditions.

According to some embodiments of the invention, the non-adherent conditions comprise a non-adherent culture plate.

According to some embodiments of the invention, the non-adherent conditions comprise a non-adherent substrate.

According to some embodiments of the invention, step (a) comprises:

i) culturing the cultured population of human pluripotent stem cells in a medium comprising nicotinamide, in the absence of activin A; under non-adherent conditions to generate a cluster of cells comprising differentiating cells; and subsequently; and ii) culturing the differentiating cells of (i) in a medium comprising nicotinamide, in the absence of activin A under adherent conditions.

According to some embodiments of the invention, the method further comprises dissociating the cluster of cells prior to step (ii) to generate clumps of cells or a single cell suspension of cells.

According to some embodiments of the invention, step (a) is effected for at least five days.

According to some embodiments of the invention, step (b) is effected for at least one week.

According to some embodiments of the invention, at least a portion of the culturing is effected under conditions wherein the atmospheric oxygen level is less than about 10%.

According to some embodiments of the invention, the culturing is effected under conditions wherein the atmospheric oxygen level is greater than about 10%.

According to some embodiments of the invention, the human pluripotent stem cells are expanded on feeder cells.

According to some embodiments of the invention, the feeder cells comprise human cord fibroblasts.

According to some embodiments of the invention, the culturing the population of cells on the adherent surface is effected for at least 3 passages.

According to some embodiments of the invention, the transplanting of the differentiated RPE cells is effected at the subretinal space of the eye.

According to some embodiments of the invention, the RPE cells are transplanted in a suspension, or as a monolayer of cells immobilized on a matrix or a substrate.

According to some embodiments of the invention, the retinal disease or disorder is selected from at least one of retinitis pigmentosa, lebers congenital amaurosis, hereditary or acquired macular degeneration, age related macular degeneration (AMD), Best disease, retinal detachment, gyrate atrophy, choroideremia, pattern dystrophy, RPE dystrophies, Stargardt disease, RPE and retinal damage due to damage caused by any one of photic, laser, inflammatory, infectious, radiation, neovascular or traumatic injury.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

The present invention, in some embodiments thereof, relates to methods of preparing retinal pigment epithelium cells from pluripotent stem cells.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Human embryonic stem cells have been proposed as a cellular source for the generation of RPE cells. Two general approaches have been used to obtain retinal pigment epithelium (RPE) cells from hESCs, spontaneous differentiation and directed differentiation. In spontaneous differentiation, hESCs in flat colonies or in embryoid bodies (EBs) are allowed to spontaneously differentiate into a population of cells containing pigmented RPE cells. The directed differentiation method uses a number of factors to drive the differentiation of hESCs to RPE cells see for example U.S. Pat. No. 8,956,866, the contents of which are incorporated herein by reference.

A key limitation of the protocol described therein is its low scale nature, which limits industrial bulk production. The final step of RPE differentiation described in U.S. Pat. No. 8,956,866 is based on mechanically isolating polygonal/pigmented RPE cells from non-pigmented cells. This approach is labor intensive and time consuming.

The present inventors now propose that purified populations of RPE cells may be obtained without performing mechanical isolation of the polygonal/pigmented cells.

Figure 9:
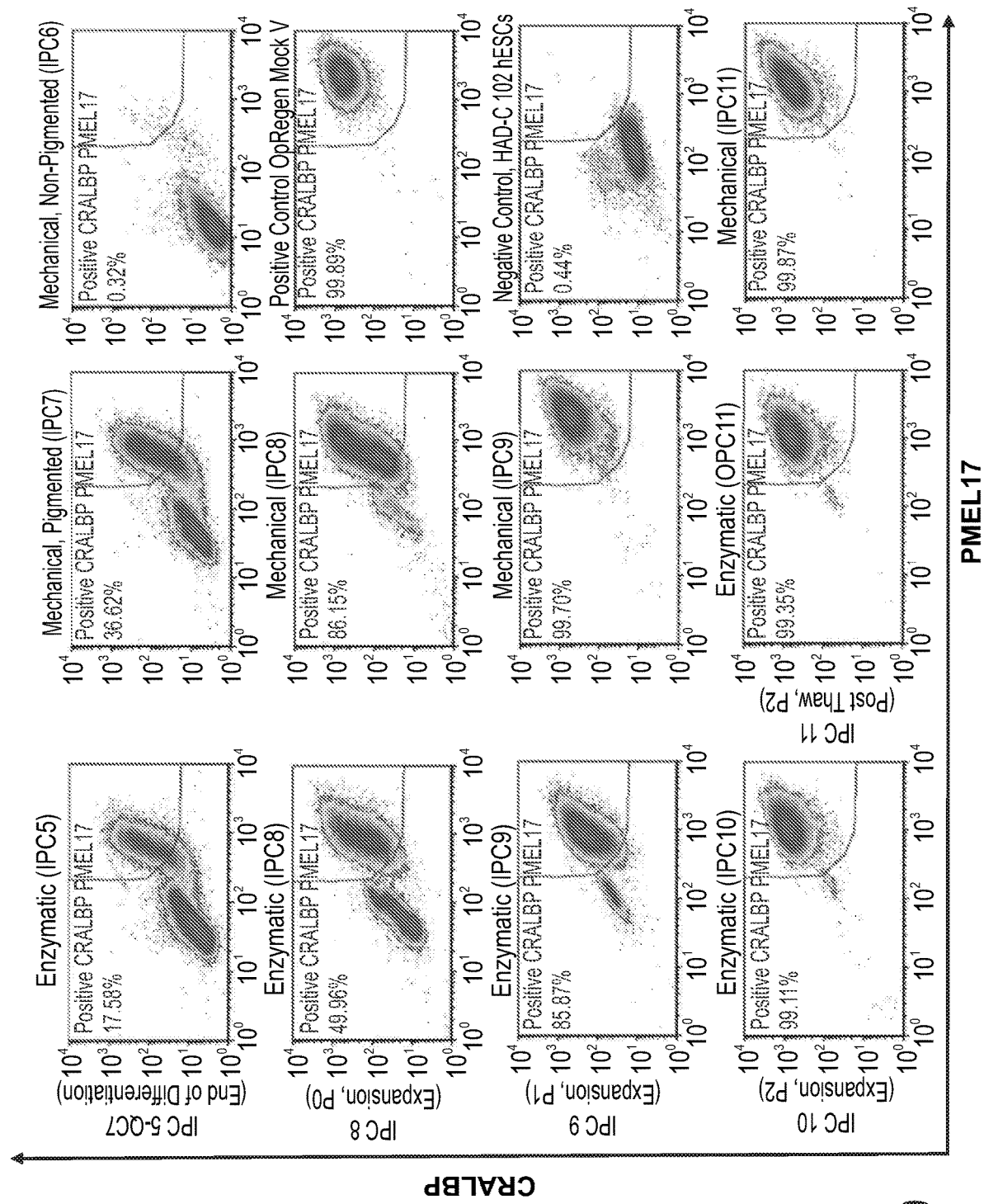
FIG. 9 illustrates % CRALBP+PMEL17+ cells along production process 2. Density plots of IPC points 5-9 and representative density plots of positive control RPE and negative control hESCs are presented. Numbers indicate percent CRALBP+PMEL17+ double positive cells out of the live single cell gated population. Analysis was performed using the FCS express 4 software.

CRALBP+PMEL17+ RPE purity testing performed following expansion of mechanically and enzymatically collected cells demonstrated that after two expansion cycles, enzymatically collected cells were as pure as mechanically isolated cells with 95.20% purity when seeded on collagen I (as compared to 97.99% when isolated mechanically), 95.02% purity when seeded on collagen IV (as compared to 96.68% when isolated mechanically) and 94.91% purity when seeded on laminin 521 (as compared to 96.41% when isolated mechanically). Similar results were seen after three expansion cycles. These results were supported by morphology testing demonstrating typical polygonal-shaped epithelial monolayer morphology and by functional testing demonstrating PEDF secretion, barrier function and polarized secretion of VEGF and PEDF. To illustrate the consistency of these findings, a second production run was performed (FIG. 9).

Thus, according to a first aspect of the present invention there is provided a method of generating retinal pigment epithelial (RPE) cells comprising:

(a) culturing a population of human pluripotent stem cells in a medium comprising a differentiating agent to obtain differentiating cells;

(b) culturing the differentiating cells in a culture comprising a medium which comprises one or more members of the TGFβ superfamily, thereby generating a mixed population of cells comprising RPE cells;

(c) removing the mixed population of cells from the culture, wherein more than 10% of the cells of the mixed population of cells are non-pigmented cells; and subsequently;

(d) culturing the mixed population of cells on an adherent surface to generate an expanded population of RPE cells; and (e) harvesting the expanded population of RPE cells, thereby generating the RPE cells.

"Retinal pigment epithelium cells", "RPE cells", "RPEs", which may be used interchangeably as the context allows, refers to cells of a cell type functionally similar to that of native RPE cells which form the pigment epithelium cell layer of the retina (e.g. upon transplantation within an eye, they exhibit functional activities similar to those of native RPE cells).

According to one embodiment, the RPE cell expresses at least one, two, three, four or five markers of mature RPE cells. Such markers include, but are not limited to CRALBP, RPE65, PEDF, PMEL17, bestrophin and tyrosinase. Optionally, the RPE cell may also express a marker of an RPE progenitor—e.g. MITF. In another embodiment, the RPE cells express PAX-6. In another embodiment, the RPE cells express at least one marker of a retinal progenitor cell including, but not limited to Rx, OTX2 or SIX3. Optionally, the RPE cells express either SIX6 and/or LHX2.

As used herein the phrase "markers of mature RPE cells" refers to antigens (e.g. proteins) that are elevated (e.g. at least 2 fold, at least 5 fold, at least 10 fold) in mature RPE cells with respect to non RPE cells or immature RPE cells.

As used herein the phrase "markers of RPE progenitor cells" refers to antigens (e.g. proteins) that are elevated (e.g. at least 2 fold, at least 5 fold, at least 10 fold) in RPE progenitor cells with respect to non RPE cells.

According to another embodiment, the RPE cells have a morphology similar to that of native RPE cells which form the pigment epithelium cell layer of the retina i.e. pigmented and having a characteristic polygonal shape.

According to still another embodiment, the RPE cells are capable of treating diseases such as macular degeneration.

According to still another embodiment, the RPE cells fulfill at least 1, 2, 3, 4 or all of the requirements listed herein above.

As used herein, the phrase "stem cells" refers to cells which are capable of remaining in an undifferentiated state (e.g., pluripotent or multipotent stem cells) for extended periods of time in culture until induced to differentiate into other cell types having a particular, specialized function (e.g., fully differentiated cells). Preferably, the phrase "stem cells" encompasses embryonic stem cells (ESCs), induced pluripotent stem cells (iPSCs), adult stem cells, mesenchymal stem cells and hematopoietic stem cells.

According to a particular embodiment, the RPE cells are generated from pluripotent stem cells (e.g. ESCs or iPSCs).

Induced pluripotent stem cells (iPSCs) can be generated from somatic cells by genetic manipulation of somatic cells, e.g., by retroviral transduction of somatic cells such as fibroblasts, hepatocytes, gastric epithelial cells with transcription factors such as Oct-3/4, Sox2, c-Myc, and KLF4 [Yamanaka S, Cell Stem Cell. 2007, 1(1):39-49; Aoi T, et al., Generation of Pluripotent Stem Cells from Adult Mouse Liver and Stomach Cells. Science. 2008 Feb. 14. (Epub ahead of print); I H Park, Zhao R, West J A, et al. Reprogramming of human somatic cells to pluripotency with defined factors. Nature 2008; 451:141-146; K Takahashi, Tanabe K, Ohnuki M, et al. Induction of pluripotent stem cells from adult human fibroblasts by defined factors. Cell 2007; 131:861-872]. Other embryonic-like stem cells can be generated by nuclear transfer to oocytes, fusion with embryonic stem cells or nuclear transfer into zygotes if the recipient cells are arrested in mitosis. In addition iPSCs may be generated using non-integrating methods e.g. using small molecules or RNA.

The phrase "embryonic stem cells" refers to embryonic cells which are capable of differentiating into cells of all three embryonic germ layers (i.e., endoderm, ectoderm and mesoderm), or remaining in an undifferentiated state. The phrase "embryonic stem cells" may comprise cells which are obtained from the embryonic tissue formed after gestation (e.g., blastocyst) before implantation of the embryo (i.e., a pre-implantation blastocyst), extended blastocyst cells (EBCs) which are obtained from a post-implantation/pre-gastrulation stage blastocyst (see WO2006/040763) and embryonic germ (EG) cells which are obtained from the genital tissue of a fetus any time during gestation, preferably before 10 weeks of gestation. The embryonic stem cells of some embodiments of the invention can be obtained using well-known cell-culture methods. For example, human embryonic stem cells can be isolated from human blastocysts. Human blastocysts are typically obtained from human in vivo preimplantation embryos or from in vitro fertilized (IVF) embryos. Alternatively, a single cell human embryo can be expanded to the blastocyst stage. For the isolation of human ES cells the zona pellucida is removed from the blastocyst and the inner cell mass (ICM) is isolated by a procedure in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 4-7 days. For further details on methods of preparation human ES cells see Reubinoff et al. Nat Biotechnol 2000, May: 18(5): 559; Thomson et al., [U.S. Pat. No. 5,843,780; Science 282: 1145, 1998; Curr. Top. Dev. Biol. 38: 133, 1998; Proc. Natl. Acad. Sci. USA 92: 7844, 1995]; Bongso et al., [Hum Reprod 4: 706, 1989]; and Gardner et al., [Fertil. Steril. 69: 84, 1998].

It will be appreciated that commercially available stem cells can also be used according to some embodiments of the invention Human ES cells can be purchased from the NIH human embryonic stem cells registry [www.grants(dot)nih (dot)gov/stem_cells/registry/current(dot)htm] or from other hESC registries. Non-limiting examples of commercially available embryonic stem cell lines are HAD-C102, ESI, BG01, BG02, BG03, BG04, CY12, CY30, CY92, CY10, TE03, TE32, CHB-4, CHB-5, CHB-6, CHB-8, CHB-9, CHB-10, CHB-11, CHB-12, HUES 1, HUES 2, HUES 3, HUES 4, HUES 5, HUES 6, HUES 7, HUES 8, HUES 9, HUES 10, HUES 11, HUES 12, HUES 13, HUES 14, HUES 15, HUES 16, HUES 17, HUES 18, HUES 19, HUES 20, HUES 21, HUES 22, HUES 23, HUES 24, HUES 25, HUES 26, HUES 27, HUES 28, CyT49, RUES3, WA01, UCSF4, NYUES1, NYUES2, NYUES3, NYUES4, NYUES5, NYUES6, NYUES7, UCLA 1, UCLA 2, UCLA 3, WA077 (H7), WA09 (H9), WA13 (H13), WA14 (H14), HUES 62, HUES 63, HUES 64, CT1, CT2, CT3, CT4, MA135, Eneavour-2, WIBR1, WIBR2, WIBR3, WIBR4, WIBR5, WIBR6, HUES 45, Shef 3, Shef 6, BJNhem19, BJNhem20, SA001, SA001.

According to a specific embodiment, the embryonic stem cell line is HAD-C102 or ESI.

In addition, ES cells can be obtained from other species as well, including mouse (Mills and Bradley, 2001), golden hamster [Doetschman et al., 1988, Dev Biol. 127: 224-7], rat

[Iannaccone et al., 1994, Dev Biol. 163: 288-92] rabbit [Giles et al. 1993, Mol Reprod Dev. 36: 130-8; Graves & Moreadith, 1993, Mol Reprod Dev. 1993, 36: 424-33], several domestic animal species [Notarianni et al., 1991, J Reprod Fertil Suppl. 43: 255-60; Wheeler 1994, Reprod Fertil Dev. 6: 563-8; Mitalipova et al., 2001, Cloning. 3: 59-67] and non-human primate species (Rhesus monkey and marmoset) [Thomson et al., 1995, Proc Natl Acad Sci USA. 92: 7844-8; Thomson et al., 1996, Biol Reprod. 55: 254-9].

Extended blastocyst cells (EBCs) can be obtained from a blastocyst of at least nine days post fertilization at a stage prior to gastrulation. Prior to culturing the blastocyst, the zona pellucida is digested [for example by Tyrode's acidic solution (Sigma Aldrich, St Louis, Mo., USA)] so as to expose the inner cell mass. The blastocysts are then cultured as whole embryos for at least nine and no more than fourteen days post fertilization (i.e., prior to the gastrulation event) in vitro using standard embryonic stem cell culturing methods.

Another method for preparing ES cells is described in Chung et al., Cell Stem Cell, Volume 2, Issue 2, 113-117, 7 Feb. 2008. This method comprises removing a single cell from an embryo during an in vitro fertilization process. The embryo is not destroyed in this process.

EG cells are prepared from the primordial germ cells obtained from fetuses of about 8-11 weeks of gestation (in the case of a human fetus) using laboratory techniques known to anyone skilled in the arts. The genital ridges are dissociated and cut into small chunks which are thereafter disaggregated into cells by mechanical dissociation. The EG cells are then grown in tissue culture flasks with the appropriate medium. The cells are cultured with daily replacement of medium until a cell morphology consistent with EG cells is observed, typically after 7-30 days or 1-4 passages. For additional details on methods of preparation human EG cells see Shamblott et al., [Proc. Natl. Acad. Sci. USA 95: 13726, 1998] and U.S. Pat. No. 6,090,622.

Yet another method for preparing ES cells is by parthenogenesis. The embryo is also not destroyed in the process.

Currently practiced ES culturing methods are mainly based on the use of feeder cell layers which secrete factors needed for stem cell proliferation, while at the same time, inhibit their differentiation. The culturing is typically effected on a solid surface—e.g. a surface coated with gelatin or vimentin. Exemplary feeder layers include Human embryonic fibroblasts, adult fallopian epithelial cells, primary mouse embryonic fibroblasts (PMEF), mouse embryonic fibroblasts (MEF), murine fetal fibroblasts (MFF), human embryonic fibroblast (HEF), human fibroblasts obtained from the differentiation of human embryonic stem cells, human fetal muscle cells (HFM), human fetal skin cells (HFS), human adult skin cells, human foreskin fibroblasts (HFF), human umbilical cord fibroblasts, human cells obtained from the umbilical cord or placenta, and human marrow stromal cells (hMSCs). Growth factors may be added to the medium to maintain the ESCs in an undifferentiated state. Such growth factors include bFGF and/or TGFβ. In another embodiment, agents may be added to the medium to maintain the hESCs in a naïve undifferentiated state—see for example Kalkan et al., 2014, Phil. Trans. R. Soc. B, 369: 20130540.

Human Umbilical Cord Feeder-Layer—

Human umbilical cord fibroblasts may be expanded in Dulbecco's Modified Eagle's Medium (e.g. DMEM, SH30081.01, Hyclone) supplemented with human serum (e.g. 20%) and glutamine. Preferably the human cord cells are irradiated. This may be effected using methods known in the art (e.g. Gamma cell, 220 Exel, MDS Nordion 3,500 rads). Once sufficient cells are obtained they may be frozen (e.g. cryopreserved). For expansion of ESCs, the human cord fibroblasts are typically seeded on a solid surface (e.g. T75 or T175 flasks) optionally coated with an adherent substrate such as gelatin (e.g. recombinant human gelatin (RhG100-001, Fibrogen) at a concentration of 25-40,000 cells/cm$^2$ in DMEM (e.g. SH30081.01, Hyclone) supplemented with about 20% human serum (and glutamine). hESCs are typically plated on top of the feeder cells 1-4 days later in a supportive medium (e.g. Nutristem with human serum albumin). Additional factors may be added to the medium to prevent differentiation of the ESCs such as bFGF and TGF-β. Once a sufficient amount of hESCs are obtained, the cells may be mechanically disrupted (e.g. by using a sterile tip or a disposable sterile stem cell tool; 14602 Swemed). Alternatively, the cells may be removed by enzymatic treatment (e.g. collagenase A, or TrypLE Select). This process may be repeated several times to reach the necessary amount of hESC. According to a particular embodiment, following the first round of expansion, the hESCs are removed using TrypLE Select and following the second round of expansion, the hESCs are removed using collagenase A.

Human Embryonic Fibroblasts or Adult Fallopian Epithelial Cells as Feeder Cell Layers—

Human ES cells can be grown and maintained using human embryonic fibroblasts or adult fallopian epithelial cells. When grown on these human feeder cells the human ES cells exhibit normal karyotypes, present alkaline phosphatase activity, express Oct-4 and other embryonic cell surface markers including SSEA-3, SSEA-4, TRA-1-60, and GCTM-2, form teratomas in vivo, and retain all key morphological pluripotent characteristics [Richards M, Fong C Y, Chan W K, Wong P C, Bongso A. (2002). Human feeders support prolonged undifferentiated growth of human inner cell masses and embryonic stem cells. Nat. Biotechnol. 20: 933-6].

Foreskin Feeder Layers—

Human ES cells can be cultured on human foreskin feeder layer as disclosed in U.S. patent application Ser. No. 10/368, 045. Foreskin derived feeder cell layers consist of a complete animal-free environment suitable for culturing human ES cells. In addition, foreskin cells can be maintained in culture for as long as 50 passages since their derivation, providing the ES cells with a relatively constant environment. Under these conditions the human ES cells were found to be functionally indistinct from cells grown with alternate protocols (e.g., MEF). Following differentiation, ES cells expressed genes associated with all three embryonal germ layers, in vitro, and formed teratomas in vivo, consisting of tissue arising from all three germ layers.

Feeder cell free systems have also been used in ES cell culturing, such systems utilize matrices supplemented with serum replacement, cytokines and growth factors (including IL6 and soluble IL6 receptor chimera) as a replacement for the feeder cell layer. Stem cells can be grown on a solid surface such as an extracellular matrix (e.g., Matrigel® or laminin) in the presence of a culture medium—for example the Lonza L7 system, mTeSR, StemPro, XFKSR, E8). Unlike feeder-based cultures which require the simultaneous growth of feeder cells and stem cells and which may result in mixed cell populations, stem cells grown on feeder-free systems are easily separated from the surface.

The ESCs may be expanded on feeders prior to the differentiation step. Exemplary feeder layer based cultures contemplated by the present invention are described herein above. The expansion is typically effected for at least two days, three days, four days, five days, six days or seven days. The expansion is effected for at least 1 passage, at least 2 passages, at least 3 passages, at least 4 passages, at least 5 passages, at least 6 passages, at least 7 passages, at least 8 passages, at least 9 passages or at least 10 passages.

Following expansion, the pluripotent stem cells (e.g. ESCs) are subjected to directed differentiation using a differentiating agent.

In one exemplary differentiation protocol, the embryonic stem cells are differentiated towards the RPE cell lineage using a first differentiating agent and then further differentiated towards RPE cells using a member of the transforming growth factor-ß (TGFß) superfamily, (e.g. TGFβ1, TGFβ2, and TGFβ3 subtypes, as well as homologous ligands including activin (e.g., activin A, activin B, and activin AB), nodal, anti-mullerian hormone (AMH), some bone morphogenetic proteins (BMP), e.g. BMP2, BMP3, BMP4, BMP5, BMP6, and BMP7, and growth and differentiation factors (GDF)). According to a specific embodiment, the member of the transforming growth factor-ß (TGFß) superfamily is activin A—e.g. between 20-200 ng/ml e.g. 100-180 ng/ml.

According to a particular embodiment, the first differentiating agent is nicotinamide (NA)—e.g. between 0.01-100 mM, 0.1-100 mM, 0.1-50 mM, 5-50 mM, 5-20 mM, e.g. 10 mM.

According to another embodiment, the first differentiating agent is 3-aminobenzamide.

NA, also known as "niacinamide", is the amide derivative form of Vitamin B3 (niacin) which is thought to preserve and improve beta cell function. NA has the chemical formula $C_6H_6N_2O$. NA is essential for growth and the conversion of foods to energy, and it has been used in arthritis treatment and diabetes treatment and prevention.

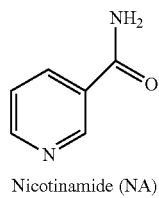

Nicotinamide (NA)

According to a particular embodiment, the nicotinamide is a nicotinamide derivative or a nicotinamide mimic. The term "derivative of nicotinamide (NA)" as used herein denotes a compound which is a chemically modified derivative of the natural NA. In one embodiment, the chemical modification may be a substitution of the pyridine ring of the basic NA structure (via the carbon or nitrogen member of the ring), via the nitrogen or the oxygen atoms of the amide moiety. When substituted, one or more hydrogen atoms may be replaced by a substituent and/or a substituent may be attached to a N atom to form a tetravalent positively charged nitrogen. Thus, the nicotinamide of the present invention includes a substituted or non-substituted nicotinamide. In another embodiment, the chemical modification may be a deletion or replacement of a single group, e.g. to form a thiobenzamide analog of NA, all of which being as appreciated by those versed in organic chemistry. The derivative in the context of the invention also includes the nucleoside derivative of NA (e.g. nicotinamide adenine). A variety of derivatives of NA are described, some also in connection with an inhibitory activity of the PDE4 enzyme (WO03/068233; WO02/060875; GB2327675A), or as VEGF-receptor tyrosine kinase inhibitors (WO01/55114). For example, the process of preparing 4-aryl-nicotinamide derivatives (WO05/014549). Other exemplary nicotinamide derivatives are disclosed in WO01/55114 and EP2128244.

Nicotinamide mimics include modified forms of nicotinamide, and chemical analogs of nicotinamide which recapitulate the effects of nicotinamide in the differentiation and maturation of RPE cells from pluripotent cells. Exemplary nicotinamide mimics include benzoic acid, 3-aminobenzoic acid, and 6-aminonicotinamide. Another class of compounds that may act as nicotinamide mimics are inhibitors of poly(ADP-ribose) polymerase (PARP). Exemplary PARP inhibitors include 3-aminobenzamide, Iniparib (BSI 201), Olaparib (AZD-2281), Rucaparib (AG014699, PF-01367338), Veliparib (ABT-888), CEP 9722, MK 4827, and BMN-673.

Additional contemplated differentiation agents include for example noggin, antagonists of Wnt (Dkk1 or IWR1e), nodal antagonists (Lefty-A), retinoic acid, taurine, GSK3b inhibitor (CHIR99021) and notch inhibitor (DAPT).

According to a particular embodiment, the differentiation is effected as follows:

a) culture of ESCs in a medium comprising a first differentiating agent (e.g. nicotinamide); and b) culture of cells obtained from step a) in a medium comprising a member of the TGFß superfamily (e.g. activin A) and the first differentiating agent (e.g. nicotinamide).

Preferably step (a) is effected in the absence of the member of the TGFß superfamily (e.g. activin A).

In one embodiment, the medium in step (a) is completely devoid of a member of the TGFß superfamily. In another embodiment, the level of TGFß superfamily member in the medium is less than 20 ng/ml, 10 ng/ml, 1 ng/ml or even less than 0.1 ng/ml.

The above described protocol may be continued by culturing the cells obtained in step b) in a medium comprising the first differentiating agent (e.g. nicotinamide), but devoid of a member of the TGFß superfamily (e.g. activin A). This step is referred to herein as step (b*).

The above described protocol is now described in further detail, with additional embodiments.

Step (a): The differentiation process is started once sufficient quantities of ESCs are obtained. They are typically removed from the cell culture (e.g. by using collagenase A, dispase, TrypLE select, EDTA) and plated onto a non-adherent substrate (e.g. cell culture plate such as Hydrocell or an agarose-coated culture dish, or petri bacteriological dishes) in the presence of nicotinamide (and the absence of activin A). Exemplary concentrations of nicotinamide are between 0.01-100 mM, 0.1-100 mM, 0.1-50 mM, 5-50 mM, 5-20 mM, e.g. 10 mM. Once the cells are plated onto the non-adherent substrate (e.g. cell culture plate), the cell culture may be referred to as a cell suspension, preferably free floating clusters in a suspension culture, i.e. aggregates of cells derived from human embryonic stem cells (hESCs). The cell clusters do not adhere to any substrate (e.g. culture plate, carrier). Sources of free floating stem cells were previously described in WO 06/070370, which is herein incorporated by reference in its entirety. This stage may be effected for a minimum of 1 day, more preferably two days, three days, 1 week or even 14 days. Preferably, the cells are not cultured for more than 3 weeks in suspension together with the nicotinamide e.g. between 0.01-100 mM, 0.1-100 mM, 0.1-50 mM, 5-50 mM, 5-20 mM, e.g. 10 mM (and in the absence of activin A). In one embodiment, the cells are cultured for 6-8 days in suspension together with the nicotinamide e.g. between 0.01-100 mM, 0.1-100 mM, 0.1-50 mM, 5-50 mM, 5-20 mM, e.g. 10 mM (and in the absence of activin A).

According to one embodiment, when the cells are cultured on the non-adherent substrate e.g. cell culture plates, the atmospheric oxygen conditions are 20%. However, manipulation of the atmospheric oxygen conditions is also contemplated such that the atmospheric oxygen percent is less than about 20%, 15%, 10%, 9%, 8%, 7%, 6% or even less than about 5% (e.g. between 1%-20%, 1%-10% or 0-5%).

According to a particular embodiment, the cells are cultured on the non-adherent substrate initially under normal atmospheric oxygen conditions and then lowered to less than normal atmospheric oxygen conditions.

Examples of non-adherent cell culture plates include those manufactured by Nunc (e.g. Hydrocell Cat No. 174912), etc.

Typically, the clusters comprise at least 50-500,000, 50-100,000, 50-50,000, 50-10,000, 50-5000, 50-1000 cells. According to one embodiment, the cells in the clusters are not organized into layers and form irregular shapes. In one embodiment, the clusters are devoid of pluripotent embryonic stem cells. In another embodiment, the clusters comprise small amounts of pluripotent embryonic stem cells (e.g. no more than 5%, or no more than 3% (e.g. 0.01-2.7%) cells that co-express OCT4 and TRA-1-60 at the protein level). Typically, the clusters comprise cells that have been partially differentiated under the influence of nicotinamide. Such cells primarily express neural and retinal precursor markers such as PAX6, Rax, Six3 and/or CHX10.

The clusters may be dissociated using enzymatic or non-enzymatic methods (e.g., mechanical) known in the art. According to one embodiment, the cells are dissociated such that they are no longer in clusters—e.g. aggregates or clumps of 2-100,000 cells, 2-50,000 cells, 2-10,000 cells, 2-5000 cells, 2-1000 cells, 2-500 cells, 2-100 cells, 2-50 cells. According to a particular embodiment, the cells are in a single cell suspension.

The cells (e.g. dissociated cells) are then plated on an adherent substrate and cultured in the presence of nicotinamide e.g. between 0.01-100 mM, 0.1-100 mM, 0.1-50 mM, 5-50 mM, 5-20 mM, e.g. 10 mM (and the absence of activin A). This stage may be effected for a minimum of 1 day, more preferably two days, three days, 1 week or even 14 days. Preferably, the cells are not cultured for more than 3 weeks in the presence of nicotinamide (and in the absence of activin). In an exemplary embodiment, this stage is effected for 6-7 days.

According to one embodiment, when the cells are cultured on the adherent substrate e.g. laminin, the atmospheric oxygen conditions are 20%. They may be manipulated such that the percentage is less than about 20%, 15%, 10%, more preferably less than about 9%, less than about 8%, less than about 7%, less than about 6% and more preferably about 5% (e.g. between 1%-20%, 1%-10% or 0-5%).

According to a particular embodiment, the cells are cultured on the adherent substrate initially under normal atmospheric oxygen conditions and then lowered to less than normal atmospheric oxygen conditions.

Examples of adherent substrates include but are not limited to fibronectin, laminin, polyD-lysine, collagen and gelatin.

Step (b): Following the first stage of directed differentiation, (step a; i.e. culture in the presence of nicotinamide (e.g. between 0.01-100 mM, 0.1-100 mM, 0.1-50 mM, 5-50 mM, 5-20 mM, e.g. 10 mM), the partially-differentiated cells are then subjected to a further stage of differentiation on an adherent substrate—culturing in the presence of activin A (e.g. 0.01-1000 ng/ml, 0.1-200 ng/ml, 1-200 ng/ml—for example 140 ng/ml, 150 ng/ml, 160 ng/ml or 180 ng/ml). Thus activin A may be added at a final molarity of 0.1 pM-10 nM, 10 pM-10 nM, 0.1 nM-10 nM, 1 nM-10 nM, for example 5.4 nM.

Nicotinamide may be added at this stage too (e.g. between 0.01-100 mM, 0.1-100 mM, 0.1-50 mM, 5-50 mM, 5-20 mM, e.g. 10 mM). This stage may be effected for 1 day to 10 weeks, 3 days to 10 weeks, 1 week to 10 weeks, one week to eight weeks, one week to four weeks, for example for at least one day, at least two days, at least three days, at least 5 days, at least one week, at least two weeks, at least three weeks, at least four weeks, at least five weeks, at least six weeks, at least seven weeks, at least eight weeks, at least nine weeks, at least ten weeks.

According to a specific embodiment this stage is effected for about two weeks. This stage of differentiation may be effected at low or normal atmospheric oxygen conditions, as detailed herein above.

Step (b*): Following the second stage of directed differentiation (i.e. culture in the presence of nicotinamide and activin A on an adherent substrate; step (b), the further differentiated cells are optionally subjected to a subsequent stage of differentiation on the adherent substrate—culturing in the presence of nicotinamide (e.g. between 0.01-100 mM, 0.1-100 mM, 0.1-50 mM, 5-50 mM, 5-20 mM, e.g. 10 mM), in the absence of activin A. This stage may be effected for at least one day, 2, days, 5 days, at least one week, at least two weeks, at least three weeks or even four weeks. Preferably this stage is effected for about one week. This stage of differentiation may also be carried out at low or normal atmospheric oxygen conditions, as detailed herein above.

The basic medium in which the ESCs are differentiated is any known cell culture medium known in the art for supporting cells growth in vitro, typically, a medium comprising a defined base solution, which includes salts, sugars, amino acids and any other nutrients required for the maintenance of the cells in the culture in a viable state. According to a specific embodiment, the basic medium is not a conditioned medium. Non-limiting examples of commercially available basic media that may be utilized in accordance with the invention comprise Nutristem (without bFGF and TGFβ for ESC differentiation, with bFGF and TGFβ for ESC expansion), Neurobasal™, KO-DMEM, DMEM, DMEM/F12, Cellgro™ Stem Cell Growth Medium, or X-Vivo™ The basic medium may be supplemented with a variety of agents as known in the art dealing with cell cultures. The following is a non-limiting reference to various supplements that may be included in the culture to be used in accordance with the present disclosure:

serum or with a serum replacement containing medium, such as, without being limited thereto, knock out serum replacement (KOSR), Nutridoma-CS, TCH™, N2, N2 derivative, or B27 or a combination;

an extracellular matrix (ECM) component, such as, without being limited thereto, fibronectin, laminin, collagen and gelatin. The ECM may then be used to carry the one or more members of the TGFß superfamily of growth factors;

an antibacterial agent, such as, without being limited thereto, penicillin and streptomycin; and non-essential amino acids (NEAA), neurotrophins which are known to play a role in promoting the survival of SCs in culture, such as, without being limited thereto, BDNF, NT3, NT4.

According to a preferred embodiment, the medium used for differentiating the ESCs is Nutristem medium (Biological Industries, 06-5102-01-1A).

According to a particular embodiment differentiation and expansion of ESCs is effected under xeno free conditions.

According to one embodiment, the proliferation/growth medium is devoid of xeno contaminants i.e. free of animal derived components such as serum, animal derived growth factors and albumin. Thus, according to this embodiment, the culturing is performed in the absence of xeno contaminants.

Other methods for culturing ESCs under xeno free conditions are provided in U.S. Patent Application No. 20130196369, the contents of which are incorporated in their entirety.

The preparations comprising RPE cells may be prepared in accordance with Good Manufacturing Practices (GMP) (e.g., the preparations are GMP-compliant) and/or current Good Tissue Practices (GTP) (e.g., the preparations may be GTP-compliant).

During differentiation steps, the embryonic stem cells may be monitored for their differentiation state. Cell differentiation can be determined upon examination of cell or tissue-specific markers which are known to be indicative of differentiation.

Tissue/cell specific markers can be detected using immunological techniques well known in the art [Thomson J A et al., (1998). Science 282: 1145-7]. Examples include, but are not limited to, flow cytometry for membrane-bound or intracellular markers, immunohistochemistry for extracellular and intracellular markers and enzymatic immunoassay, for secreted molecular markers.

Following the stages of differentiation described herein above, a mixed cell population is obtained comprising both pigmented and non-pigmented cells.

According to this aspect of the present invention, the cells of the mixed cell population are removed from the plate.

In one embodiment, this is effected enzymatically (e.g. using trypsin, (TrypLE Select)). According to this aspect of the present invention, at least 10%, 20%, 30%, at least 40%, at least 50%, at least 60%, at least 70% of the cells which are removed from the culture (and subsequently expanded) are non-pigmented cells.

In another embodiment, this is effected mechanically—e.g. using a cell scraper.

In yet another embodiment, this is effected chemically (e.g. EDTA).

Combinations of enzymatic and chemical treatment are also contemplated for example EDTA and enzymatic treatment.

Furthermore, at least 10%, 20% or even 30% of the cells which are removed from the culture (and subsequently expanded) are pigmented cells.

According to this aspect of the present invention, at least 50%, 60%, 70%, 80%, 90%, 95%, 100% of all the cells in the culture are removed (and subsequently expanded).

Expansion of the mixed population of cells may be effected on an extra cellular matrix, e.g. gelatin, collagen I, collagen IV, laminin (e.g. laminin 521), fibronectin and poly-D-lysine. For expansion, the cells may be cultured in serum-free KOM, serum comprising medium (e.g. DMEM with 20% human serum) or Nutristem medium (06-5102-01-1A, Biological Industries). Under these culture conditions, after passaging under suitable conditions, the ratio of pigmented cells:non-pigmented cells increases such that a population of purified RPE cells is obtained. Such cells show the characteristic polygonal shape morphology and pigmentation of RPE cells.

In one embodiment, the expanding is effected in the presence of nicotinamide (e.g. between 0.01-100 mM, 0.1-100 mM, 0.1-50 mM, 5-50 mM, 5-20 mM, e.g. 10 mM), and in the absence of activin A.

The mixed population of cells may be expanded in suspension (with or without a micro-carrier) or in a monolayer. The expansion of the mixed population of cells in monolayer cultures or in suspension culture may be modified to large scale expansion in bioreactors or multi/hyper stacks by methods well known to those versed in the art.

According to one embodiment, the expansion phase is effected for at least one week, at least 2 weeks, at least 3 weeks, at least 4 weeks, at least 5 weeks, at least 6 weeks, at least 7 weeks, at least 8 weeks, at least 9 weeks or even 10 weeks. Preferably, the expansion phase is effected for 1 week-10 weeks, more preferably 2 weeks-10 weeks, more preferably, 3 weeks-10 weeks, more preferably 4 weeks-10 weeks, or 4 weeks-8 weeks.

According to still another embodiment, the mixed population of cells are passaged at least 1 time during the expansion phase, at least twice during the expansion phase, at least three times during the expansion phase, at least four times during the expansion phase, at least five times during the expansion phase, or at least six times during the expansion phase.

The present inventors have shown that when cells are collected enzymatically, it is possible to continue the expansion for more than 8 passages, more than 9 passages and even more than 10 passages (e.g. 11-15 passages). The number of total cell doublings can be increased to greater than 30, e.g. 31, 32, 33, 34 or more.

The population of RPE cells generated according to the methods described herein may be characterized according to a number of different parameters.

Thus, for example, the RPE cells obtained may be polygonal in shape and pigmented.

Harvesting of the expanded population of RPE cells may be effected using methods known in the art (e.g. using an enzyme such as trypsin, or chemically using EDTA etc).

Following harvesting, the expanded population of RPE cells may optionally be cryopreserved using methods known in the art. Examples of media suitable for cryopreservation include but are not limited to 90% Human Serum/10% DMSO, CryoStor 10%, 5% and 2%, Stem Cell Banker and Prime XV® FreezIS.

It will be appreciated that the cell populations disclosed herein are devoid of undifferentiated human embryonic stem cells. According to one embodiment, less than 1:250,000 cells are Oct4$^+$TRA-1-60$^+$ cells, as measured for example by FACS. The cells also have down regulated (by more than 5,000 fold) expression of GDF3 or TDGF as measured by PCR—see for example FIG. 10.

The RPE cells of this aspect of the present invention do not express embryonic stem cell markers. Said one or more embryonic stem cell markers may comprise OCT-4, NANOG, Rex-1, alkaline phosphatase, Sox2, TDGF-beta, SSEA-3, SSEA-4, TRA-1-60, and/or TRA-1-81.

The RPE preparations may be substantially purified, with respect to non-RPE cells, comprising at least about 75%, 80%, 85%, 90%, 91%, 92%, 93%, 94%, 95%, 96%, 97%, 98%, 99%, or 100% RPE cells. The RPE cell preparation may be essentially free of non-RPE cells or consist of RPE cells. For example, the substantially purified preparation of RPE cells may comprise less than about 25%, 20%, 15%, 10%, 9%, 8%, 7%, 6%, 5%, 4%, 3%, 2%, or 1% non-RPE cell type. For example, the RPE cell preparation may comprise less than about 25%, 20%, 15%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% non-RPE cells.

The RPE cell preparations may be substantially pure, both with respect to non-RPE cells and with respect to RPE cells of other levels of maturity. The preparations may be substantially purified, with respect to non-RPE cells, and enriched for mature RPE cells. For example, in RPE cell preparations enriched for mature RPE cells, at least about 30%, 40%, 45%, 50%, 55%, 60%, 65%, 70%, 75%, 80%, 85%, 90%, 91%, 92%, 93%, 94%, 95%, 96%, 97%, 98%, 99%, 99%, or 100% of the RPE cells are mature RPE cells. The preparations may be substantially purified, with respect to non-RPE cells, and enriched for differentiated RPE cells rather than mature RPE cells. For example, at least about 30%, 40%, 45%, 50%, 55%, 60%, 65%, 70%, 75%, 80%, 85%, 90%, 91%, 92%, 93%, 94%, 95%, 96%, 97%, 98%, 99%, or 100% of the RPE cells may be differentiated RPE cells rather than mature RPE cells.

The preparations described herein may be substantially free of bacterial, viral, or fungal contamination or infection, including but not limited to the presence of HIV I, HIV 2, HBV, HCV, HAV, CMV, HTLV 1, HTLV 2, parvovirus B19, Epstein-Barr virus, or herpesvirus 1 and 2, SV40, HHV5, 6, 7, 8, CMV, polyoma virus, HPV, Enterovirus. The preparations described herein may be substantially free of *mycoplasma* contamination or infection.

Another way of characterizing the cell populations disclosed herein is by marker expression. Thus, for example, at least 80%, 85%, 90%, 95% or 100% of the cells express Bestrophin 1, as measured by immunostaining. According to one embodiment, between 80-100% of the cells express bestrophin 1.

According to another embodiment, at least 80%, 85%, 87%, 89%, 90%, 95%, 97% or 100% of the cells express Microphthalmia-associated transcription factor (MITF), as measured by immunostaining. For example, between 80-100% of the cells express MITF.

According to another embodiment, at least 80%, 85%, 87%, 89%, 90%, 95%, 97% or 100% of the cells express both Microphthalmia-associated transcription factor (MITF) and bestrophin 1, as measured by immunostaining. For example, between 80-100% of the cells co-express MITF and bestrophin 1.

According to another embodiment, at least 80%, 85%, 87%, 89%, 90%, 95%, 97% or 100% of the cells express both Microphthalmia-associated transcription factor (MITF) and ZO-1, as measured by immunostaining. For example, between 80-100% of the cells co-express MITF and ZO-1.

According to another embodiment, at least 80%, 85%, 87%, 89%, 90%, 95%, 97% or 100% of the cells express both ZO-1 and bestrophin 1, as measured by immunostaining. For example, between 80-100% of the cells co-express ZO-1 and bestrophin 1.

Figure 11:
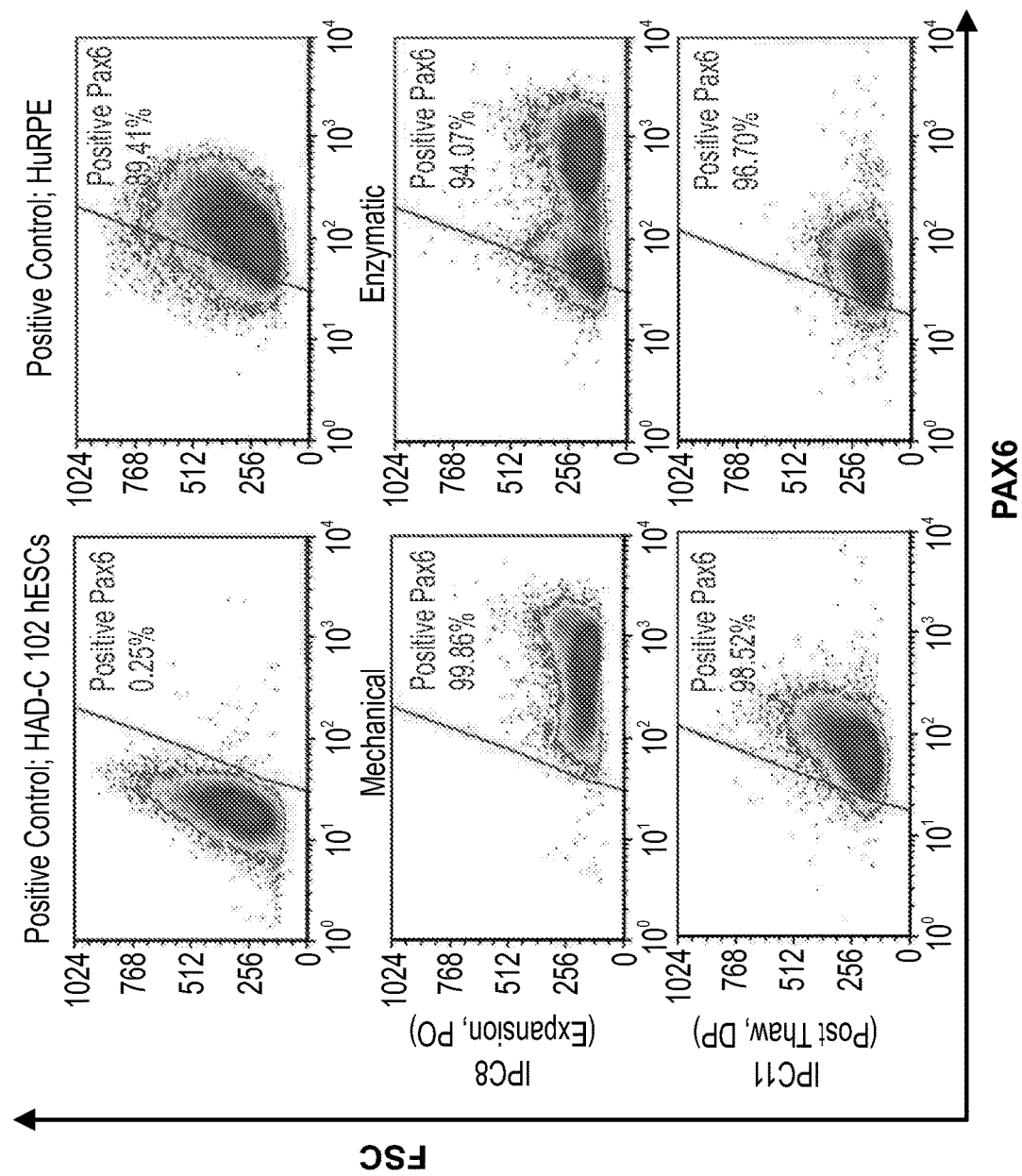
FIG. 11 illustrates % Pax6+ cells along production process 2. Density plots of IPC points 8 and 11, and representative density plots of positive control RPE and negative control hESCs are presented. Numbers indicate percent Pax6+ positive cells out of the live single cell gated population.

According to another embodiment, at least 50%, 60% 70% 80%, 85%, 87%, 89%, 90%, 95%, 97% or 100% of the cells express paired box gene 6 (PAX-6) as measured by immunostaining or FACS—see for example FIG. 11.

According to another embodiment, at least 80%, 85%, 87%, 89%, 90%, 95%, 97% or 100% of the cells express cellular retinaldehyde binding protein (CRALBP), as measured by immunostaining. For example, between 85-100% of the cells express CRALBP.

According to another embodiment, at least 80%, 85%, 87%, 89%, 90%, 95%, 97% or 100% of the cells express retinal pigment epithelium-specific protein 65 kDa (RPE65), as measured by immunostaining. For example, between 80-100% of the cells express RPE65.

The RPE cells typically co-express markers indicative of terminal differentiation, e.g. bestrophin 1, CRALBP and/or RPE65.

Following the expansion phase cell populations comprising RPE cells are obtained whereby at least 70%, 71%, 72%, 73%, 74%, 75%, 76%, 77%, 78%, 79, 80%, 81%, 82%, 83%, 84%, 85%, 86%, 87%, 88%, 89, 90%, 91%, 92%, 93%, 94%, 95%, 96%, 97%, 98%, 99 or even 100% thereof are CRALBP$^+$PMEL17$^+$.

It would be well appreciated by those versed in the art that the derivation of RPE cells is of great benefit. They may be used as an in vitro model for the development of new drugs to promote their survival, regeneration and function. RPE cells may serve for high throughput screening for compounds that have a toxic or regenerative effect on RPE cells. They may be used to uncover mechanisms, new genes, soluble or membrane-bound factors that are important for the development, differentiation, maintenance, survival and function of photoreceptor cells.

The RPE cells may also serve as an unlimited source of RPE cells for transplantation, replenishment and support of malfunctioning or degenerated RPE cells in retinal degenerations and other degenerative disorders. Furthermore, genetically modified RPE cells may serve as a vector to carry and express genes in the eye and retina after transplantation.

Eye conditions for which the RPE cells may serve as therapeutics include, but are not limited to retinal diseases or disorders generally associated with retinal dysfunction, retinal injury, and/or loss of retinal pigment epithelium. A non-limiting list of conditions which may be treated in accordance with the invention comprises retinitis pigmentosa, lebers congenital amaurosis, hereditary or acquired macular degeneration, age related macular degeneration (AMD), dry AMD, Best disease, retinal detachment, gyrate atrophy, choroideremia, pattern dystrophy as well as other dystrophies of the RPE, Stargardt disease, RPE and retinal damage due to damage caused by any one of photic, laser, inflammatory, infectious, radiation, neo vascular or traumatic injury.

Exemplary degenerative disorders that may be treated using the cells of this aspect of the present invention include neurodegenerative disorders including but not limited to Parkinson's, ALS, Multiple Sclerosis, Huntingdon's disease, autoimmune encephalomyelitis, diabetic neuropathy, Alzheimer's and epilepsy.

Subjects which may be treated include primate (including humans), canine, feline, ungulate (e.g., equine, bovine, swine (e.g., pig)), avian, and other subjects. Humans and non-human animals having commercial importance (e.g., livestock and domesticated animals) are of particular interest. Exemplary mammals which may be treated include, canines; felines; equines; bovines; ovines; rodentia, etc. and primates, particularly humans. Non-human animal models, particularly mammals, e.g. primate, murine, lagomorpha, etc. may be used for experimental investigations.

The RPE cells generated as described herein may be transplanted to various target sites within a subject's eye or other locations (for example in the brain). In accordance with one embodiment, the transplantation of the RPE cells is to the subretinal space of the eye, which is the normal anatomical location of the RPE (between the photoreceptor outer segments and the choroid). In addition, dependent upon migratory ability and/or positive paracrine effects of the cells, transplantation into additional ocular compartments can be considered including the vitreal space, inner or outer retina, the retinal periphery and within the choroids.

The number of viable cells that may be administered to the subject are typically between 50,000-5×10$^6$ per injection.

The cells are typically formulated in a carrier (e.g. an isotonic solution and/or a saline) such as BSS Plus™. Other contemplated solutions include cryopreservation solutions such as Cryostor 5 or Cryostor 2. The carrier may optionally comprise additional factors that support RPE engraftment, integration, survival, potency etc.

The transplantation may be performed by various techniques known in the art. Methods for performing RPE transplants are described in, for example, U.S. Pat. Nos. 5,962,027, 6,045,791, and 5,941,250 and in Eye Graefes Arch Clin Exp Opthalmol March 1997; 235(3):149-58; Biochem Biophys Res Commun Feb. 24, 2000; 268(3): 842-6; Opthalmic Surg February 1991; 22(2): 102-8. Methods for performing corneal transplants are described in, for example, U.S. Pat. No. 5,755,785, and in Eye 1995; 9 (Pt 6 Su):6-12; Curr Opin Opthalmol August 1992; 3 (4): 473-81; Ophthalmic Surg Lasers April 1998; 29 (4): 305-8; Ophthalmology April 2000; 107 (4): 719-24; and Jpn J Ophthalmol November-December 1999; 43(6): 502-8. If mainly paracrine effects are to be utilized, cells may also be delivered and maintained in the eye encapsulated within a semi-permeable container, which will also decrease exposure of the cells to the host immune system (Neurotech USA CNTF delivery system; PNAS Mar. 7, 2006 vol. 103(10) 3896-3901).

The step of administering may comprise intraocular administration of the RPE cells into an eye in need thereof. The intraocular administration may comprise injection of the RPE cells into the subretinal space.

In accordance with one embodiment, transplantation is performed via pars plana vitrectomy surgery followed by delivery of the cells through a small retinal opening into the sub-retinal space or by direct injection.

The RPE cells may be transplanted in various forms. For example, the RPE cells may be introduced into the target site in the form of single cell suspension, with matrix or adhered onto a matrix or a membrane, extracellular matrix or substrate such as a biodegradable polymer or a combination. The RPE cells may also be transplanted together (co-transplantation) with other retinal cells, such as with photoreceptors.

The effectiveness of treatment may be assessed by different measures of visual and ocular function and structure, including, among others, best corrected visual acuity (BCVA), retinal sensitivity to light as measured by perimetry or microperimetry in the dark and light-adapted states, full-field, multi-focal, focal or pattern electroretinography ERG), contrast sensitivity, reading speed, color vision, clinical biomicroscopic examination, fundus photography, optical coherence tomography (OCT), fundus auto-fluorescence (FAF), infrared and multicolor imaging, fluorescein or ICG angiography, adoptive optics and additional means used to evaluate visual function and ocular structure.

The subject may be administered corticosteroids prior to or concurrently with the administration of the RPE cells, such as prednisolone or methylprednisolone, Predforte.

According to another embodiment, the subject is not administered corticosteroids prior to or concurrently with the administration of the RPE cells, such as prednisolone or methylprednisolone, Predforte.

Immunosuppressive drugs may be administered to the subject prior to, concurrently with and/or following treatment.

The immunosuppressive drug may belong to the following classes:

Glucocorticoids, Cytostatics (e.g. alkylating agent or anti-metabolite), antibodies (polyclonal or monoclonal), drugs acting on immunophilins (e.g. cyclosporin, Tacrolimus or Sirolimus). Additional drugs include interferons, opioids, TNF binding proteins, mycophenolate and small biological agents.

Examples of immunosuppressive drugs include: mesenchymal stem cells, anti-lymphocyte globulin (ALG) polyclonal antibody, anti-thymocyte globulin (ATG) polyclonal antibody, azathioprine, BAS1 L1X1MAB® (anti-I L-2Ra receptor antibody), cyclosporin (cyclosporin A), DACLIZUMAB® (anti-I L-2Ra receptor antibody), everolimus, mycophenolic acid, RITUX1MAB® (anti-CD20 antibody), sirolimus, tacrolimus, Tacrolimus and or Mycophenolate mofetil.

Antibiotics may be administered to the subject prior to, concurrently with and/or following treatment. Examples of antibiotics include Oflox, Gentamicin, Chloramphenicol, Tobrex, Vigamox or any other topical antibiotic preparation authorized for ocular use.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A Laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, C A (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

This Example analyzes the effect of no-mechanical selection of RPE cells generated as described below.

Materials and Methods

Figure 1A:
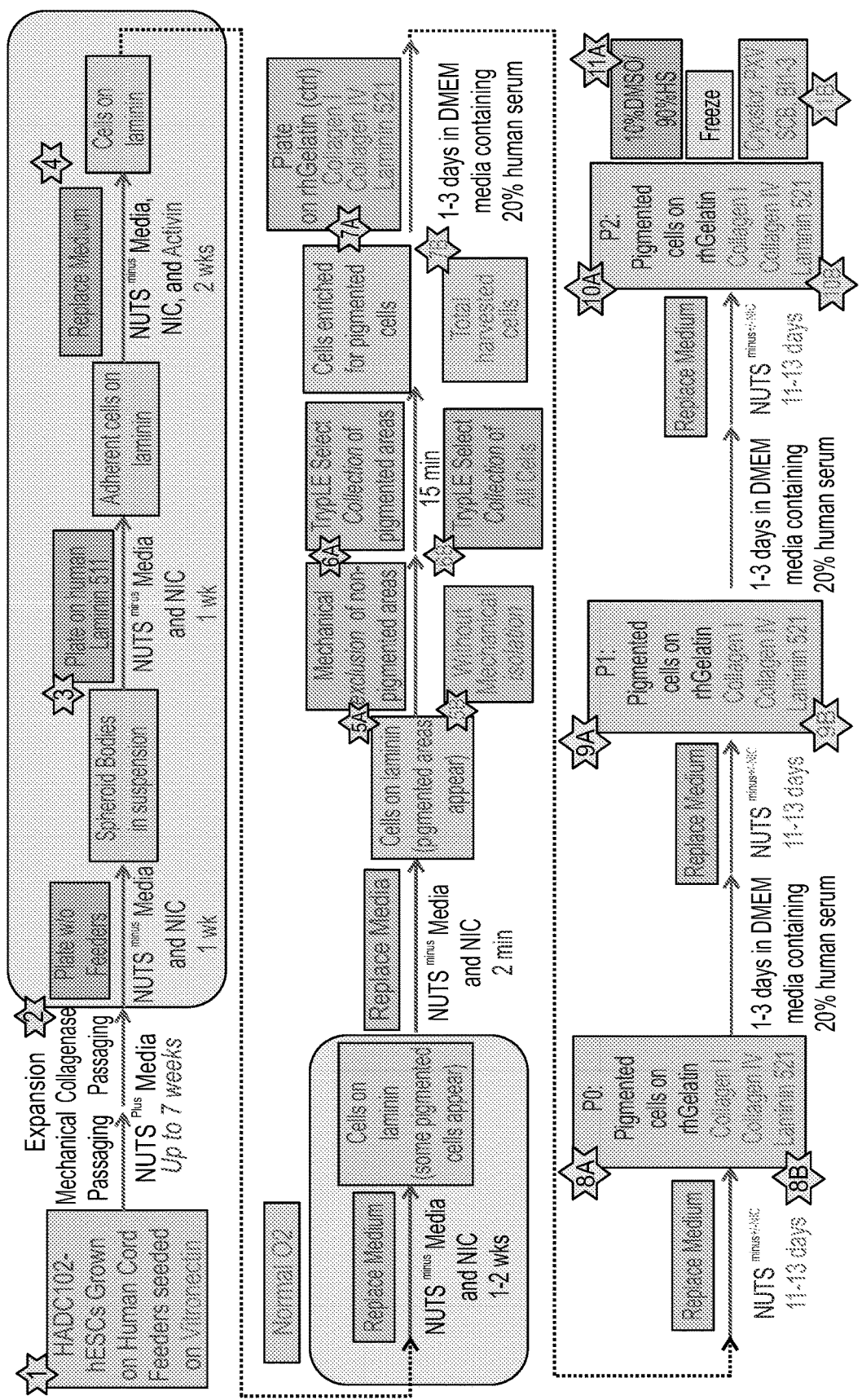
FIG. 1A is an outline of the RPE manufacturing process and in-process control points for Example 1 (yellow stars, In Process Controls, IPCs 1-11). NUTS$^{Plus}$, Nutristem medium containing bFGF and TGFβ; NUTS$^{Minus}$, Nutristem medium w/o bFGF and TGFβ; NIC, Nicotinamide; SBs, Spheroid bodies.

Generation of RPE Cells:

xeno-free GMP grade HAD-C 102 hESCs were expanded as colonies on irradiated xeno-free GMP-grade CRD008 hUCFs that were seeded on recombinant human vitronectin (rhVTN). hESC expansion was carried out in the presence of Nutristem medium that contains human serum albumin in addition to the growth factors basic FGF and TGF beta (Biological Industries 05-100-1A). Expanded hESCs were then transferred to a suspension culture to initiate differentiation in a directed manner under normal $O_2$ conditions. Spheroid bodies (SBs) were formed and then plated as an adherent cell culture under continued directed differentiation conditions towards a neural fate and subsequently towards an RPE cell fate (FIG. 1). At the end of the differentiation phase, cells were harvested using the following two techniques and expanded 1) Non-pigmented areas were manually excised and removed and the remained pigmented cell areas were enzymatically collected and 2) Cells (pigmented and non-pigmented) were collected enzymatically. Cells were then seeded and expanded for 3 passages on top of rhGelatin covered cell culture plates according to manufacturing instructions in the presence and absence of nicotinamide or on top of Laminin 521, Collagen I or Collagen IV. Cells were harvested and cryopreserved at passage 2 (P2) in cryo-medium composed of 90% human serum and 10% DMSO according to current SOP, and in various serum free xeno-free GMP grade cryo-media (CryoStor CS5 and CS10, BioLife Solutions; Stem Cell Banker AMSBIO; Prime-XV FreeIS DMSO Free, Irvine Scientific; BI1 BI2 and BI3, Biological Industries).

Results

Figure 2:
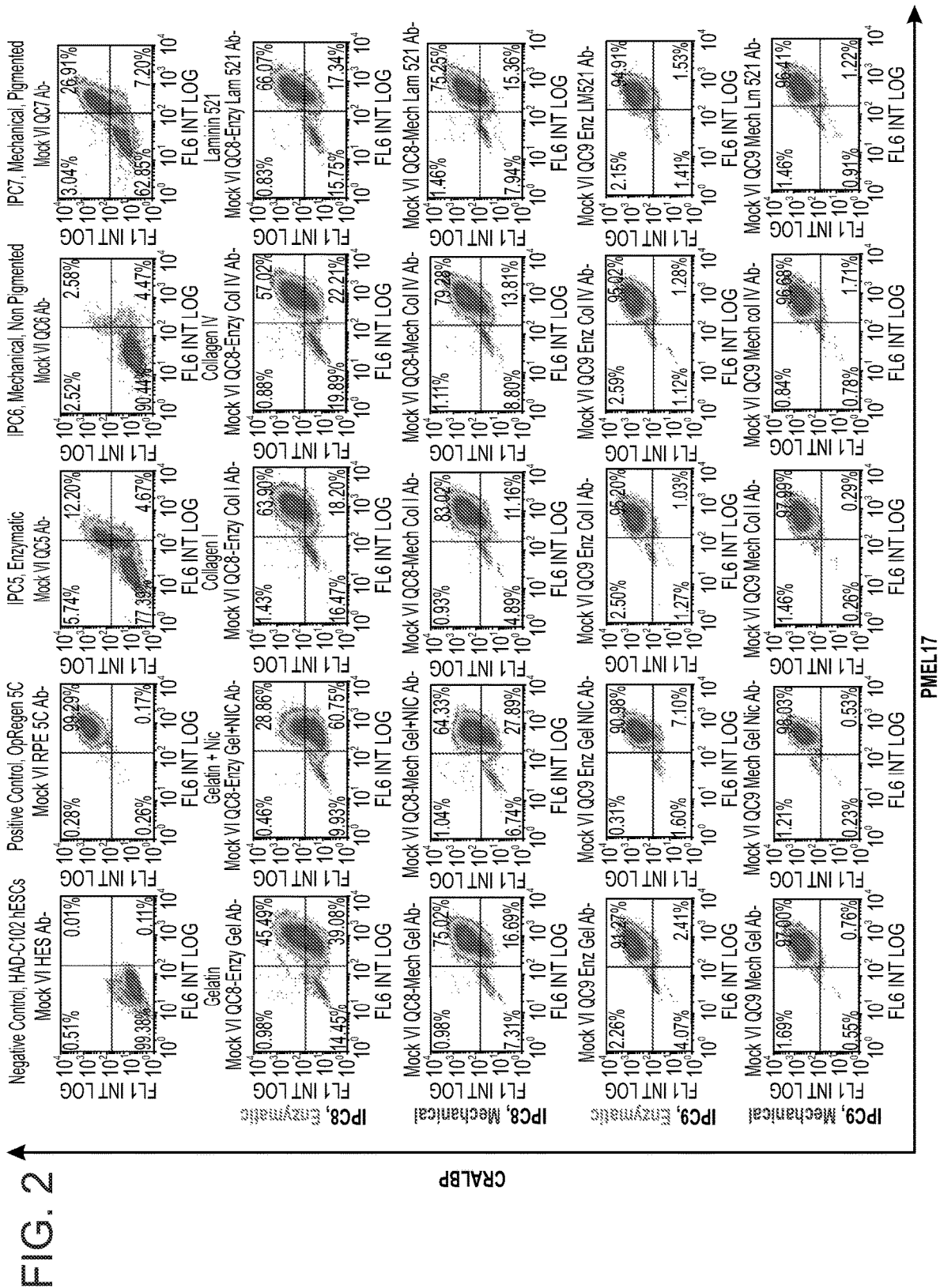
FIG. 2 illustrates the level of CRALBP+PMEL17+ cells along production process 1. Density plots of IPC points 5-9 and representative density plots of positive control RPE cells and negative control hESCs. Numbers within upper right and lower right quadrant in each plot indicate percent CRALBP+PMEL17+ and CRALBP+PMEL17− cells, respectively, out of the live single cell gated population. Analysis was done using the FCS express 4 software.
Figure 3:
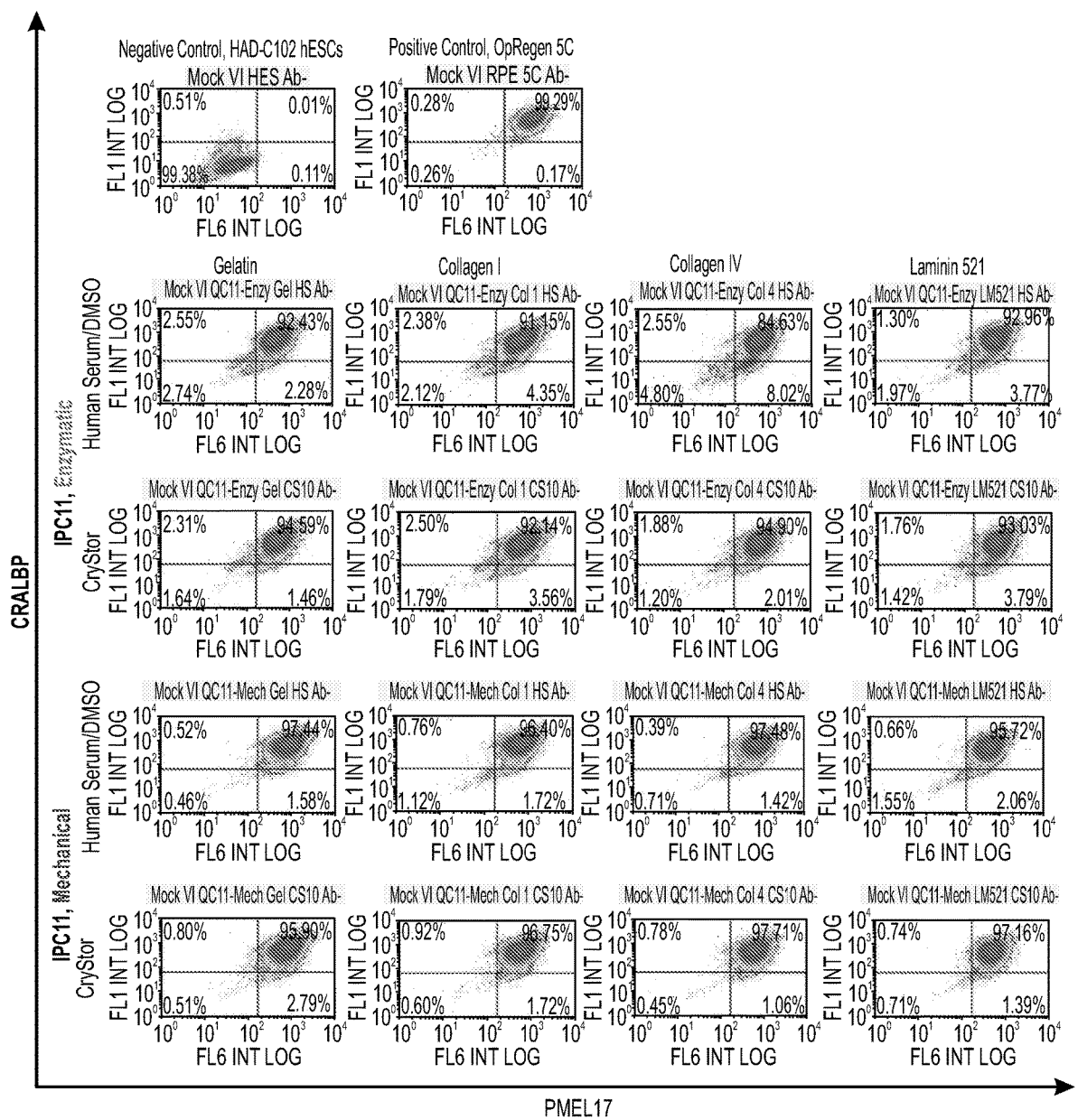
FIG. 3 illustrates the level of CRALBP+PMEL17+ Cells in the Drug Product. Density plots of IPC point 11 (Drug Product, RPE at P2 post cryopreservation) and representative density plots of positive control RPE and negative control hESCs. Numbers within upper right quadrant in each plot indicate percent CRALBP+PMEL17+ out of the live single cell gated population. Analysis was done using the FCS express 4 software.

CRALBP/PMEL17 RPE Purity along the Production Process:

HAD-C 102 hESCs grown on CRD008 hUCFs seeded on rhVTN were differentiated to RPE. At the end of the differentiation phase, cells grown on laminin 511 were harvested in two ways: 1) Mechanically, where non-pigmented/non-polygonal areas were excluded mechanically and then pigmented/polygonal area were collected enzymatically by TrypLE Select and 2) Enzymatically, where all culture containing polygonal/pigmented cells and non-polygonal/non-pigmented cells was treated with TrypLE and all cells were collected. Cells were then seeded for expansion on rhGelatin with and without (control) nicotinamide as well as on other matrixes (Laminin 521, collagen I and collagen IV). Assessment of CRALBP$^+$PMEL17$^+$ cells for measurement of RPE purity was performed at the end of the differentiation phase following enzymatic and mechanical isolation (In Process Controls, IPCs, 5-7), at P0 (IPC 8) and at P2 post cryopreservation (IPC 11). As can be seen in FIG. 2 and in Table 1, the level of CRALBP$^+$PMEL17$^+$ RPE purity at the end of the differentiation phase was 12.2% following enzymatic collection of all cells (IPC point 5) and 26.91% following mechanical isolation of polygonal/pigmented cells (IPC point 7). The areas of non-polygonal/non-pigmented cells that were isolated mechanically (IPC point 6) contained only 2.58% CRALBP⁺PMEL17+ double positive cells, as expected. Following one expansion cycle on various matrixes (P0, IPC point 8; two stages prior to the end of the production process), the level CRALBP⁺PMEL17+ double positive cells was in the range of 28.86%-66.07% when all cells were collected enzymatically and in the range of 64.33%-83.02% when polygonal/pigmented cells were isolated mechanically. After two expansion cycles, at P1 (IPC point 9), there was no major difference in the level of CRALBP$^+$PMEL17$^+$ RPE purity in cultures originating from mechanically and enzymatically treated cells especially when cells were seeded on collagen I (95.20% in enzymatically and 97.99% in mechanically collected cells), collagen IV (95.02% in enzymatically and 96.68% in mechanically collected cells) and laminin 521 (94.91% in enzymatically and 96.41% in mechanically collected cells). Similar results were seen at P2 (Drug Product, IPC point 11) especially when cells at the end of the differentiation process were cryopreserved in CryoStor 5% (for details see FIGS. 2 and 3 and Table 1).

PEDF Secretion and Potency Measurement along the Production Process:

Pigment epithelium-derived factor (PEDF), known to be secreted from RPE cells, was measured in the cell culture medium at various IPC points along the expansion phase of the production process. As can be seen in Table 2, PEDF secretion at the end of P0 (IPC point 8) was in the range 1,846-2,698 ng/mL/day in cell cultures originating from mechanically isolated polygonal/pigmented cells grown on various matrixes. In cell cultures originating from enzymatically collected cells that were grown on various matrixes the range was 212-1,113 ng PEDF/mL/day. At the end of P1 (IPC point 9; after two expansion cycles), the level of secreted PEDF was in the range of 7,779-13,067 ng/mL/day in cell cultures originating from mechanically isolated pigmented cells grown on various matrixes. In cell cultures originating from enzymatically collected cells that were grown on various matrixes the range was 4,251-9,347 ng PEDF/mL/day.

At the end of P2 prior to cryopreservation (Drug Substance, IPC point 10) PEDF secretion was similar in the two treatment groups (i.e. cell cultures originating from mechanically isolated polygonal/pigmented cells and enzymatically collected cells).

TABLE 1

Level of CRALBP⁺PMEL17⁺ Cells along the Production Process.

| | | | % CRALBP/PMEL17 RPE Purity Along the Production Process | | | | | | | | | |
|---|---|---|---|---|---|---|---|---|---|---|---|---|
| | | | Mechanical Isolation | | | | | Enzymatic Isolation | | | | |
| IPC Point Sampling Time and Stage | | | rhGelatin | rhGelatin + Nic | Collagen I | Collagen IV | Laminin 521 | rhGelatin | rhGelatin + Nic | Collagen I | Collagen IV | Laminin 521 |
| IPC | Week | Stage | | | | | | | | | | |
| 1 | 0 | Mechanically passaged hESCs | NA | NA | NA | NA | NA | NA | NA | NA | NA | NA |
| | 2 | | NA | NA | NA | NA | NA | NA | NA | NA | NA | NA |
| 2 | 3 | Collagenase passaged hESCs | NA | NA | NA | NA | NA | NA | NA | NA | NA | NA |
| 3 | 4 | Spheroid Bodies | NA | NA | NA | NA | NA | NA | NA | NA | NA | NA |
| 4 | 7 | Cells at the end of Activin A | NA | NA | NA | NA | NA | NA | NA | NA | NA | NA |
| 5 | 10 | Cells at the end of differentiation | | | NA | | | | | 12.2 | | |
| 6 | 10 | Non-Pigmented cells | | | 2.58 | | | | | NA | | |
| 7 | 10 | Pigmented cells | | | 26.91 | | | | | NA | | |
| 8 | 12 | Pigmented cells at P0 | 75.02 | 64.33 | 83.02 | 76.28 | 75.25 | 45.49 | 28.86 | 63.90 | 57.02 | 66.07 |
| 9 | 14 | Pigmented cells P1 | 97.00 | 98.03 | 97.99 | 96.68 | 96.41 | 91.27 | 90.98 | 95.20 | 95.02 | 94.91 |
| 10 | 16 | OpRegen ® (P2); DS | | | | | | | | | | |
| 11 | 28 | OpRegen ® (P2); DP¹  Cryo-media HS/DMSO | 97.44 | 95.85 | 96.40 | 97.48 | 95.72 | 92.43 | ND | 91.15 | 84.63 | 92.96 |
| | | Cryostor 5% | 95.90 | 91.72 | 96.75 | 97.71 | 97.16 | 94.59 | ND | 92.14 | 94.90 | 93.03 |

DS, drug substance;
DP, drug product;
IPC, In Process Control;
NA, Not Applicable;
ND, Not Done;
P, Passage.

TABLE 2

PEDF Secretion along the Productions Process

PEDF secretion (ng/mL/day)

| IPC Point Sampling Time and Stage | | | Mechanical Isolation | | | | | Enzymatic Isolation | | | | |
|---|---|---|---|---|---|---|---|---|---|---|---|---|
| IPC | Week | Stage | rhGelatin | rhGelatin + Nic | Collagen I | Collagen IV | Laminin 521 | rhGelatin | rhGelatin + Nic | Collagen I | Collagen IV | Laminin 521 |
| 1 | 0 | Mechanically passaged hESCs | | NA | | | | | NA | | | |
| 2 | 3 | Collagenase passaged hESCs | | NA | | | | | NA | | | |
| 3 | 4 | Spheroid Bodies | | NA | | | | | NA | | | |
| 4 | 7 | Cells at the end of Activin A | | NA | | | | | NA | | | |
| 5 | 10 | Cells at the end of differentiation | | ND[1] | | | | | ND[1] | | | |
| 6 | 10 | Non-Pigmented cells | | NA | | | | | NA | | | |
| 7 | 10 | Pigmented cells | | NA | | | | | NA | | | |
| 8 | 12 | Cells at P0 | 1,916 | 2,141 | 1,846 | 2,079 | 2,698 | 212 | 599 | 592 | 927 | 1,113 |
| 9 | 14 | Cells at P1 | 13,067 | 9,250 | 9,574 | 9,178 | 7,779 | 4,251 | 9,347 | 9,298 | 6,639 | 7,317 |
| 10 | 16 | OpRegen ® (P2); DS | ND[1] | 7,438 | 7,253 | 8,227 | 7,407 | 6,912 | ND[2] | 9,917 | 9,128 | 9,160 |
| 11 | 28 | OpRegen ® (P2); DP HS/DMSO | 7,708 | NA | NA | NA | 7,239 | 6,834 | NA | NA | NA | 5,698 |

DS, drug substance;
DP, drug product;
IPC, In Process Control;
NA, Not Applicable;
ND, Not Done;
P, Passage;
TBD, To be determined.

Figure 4:
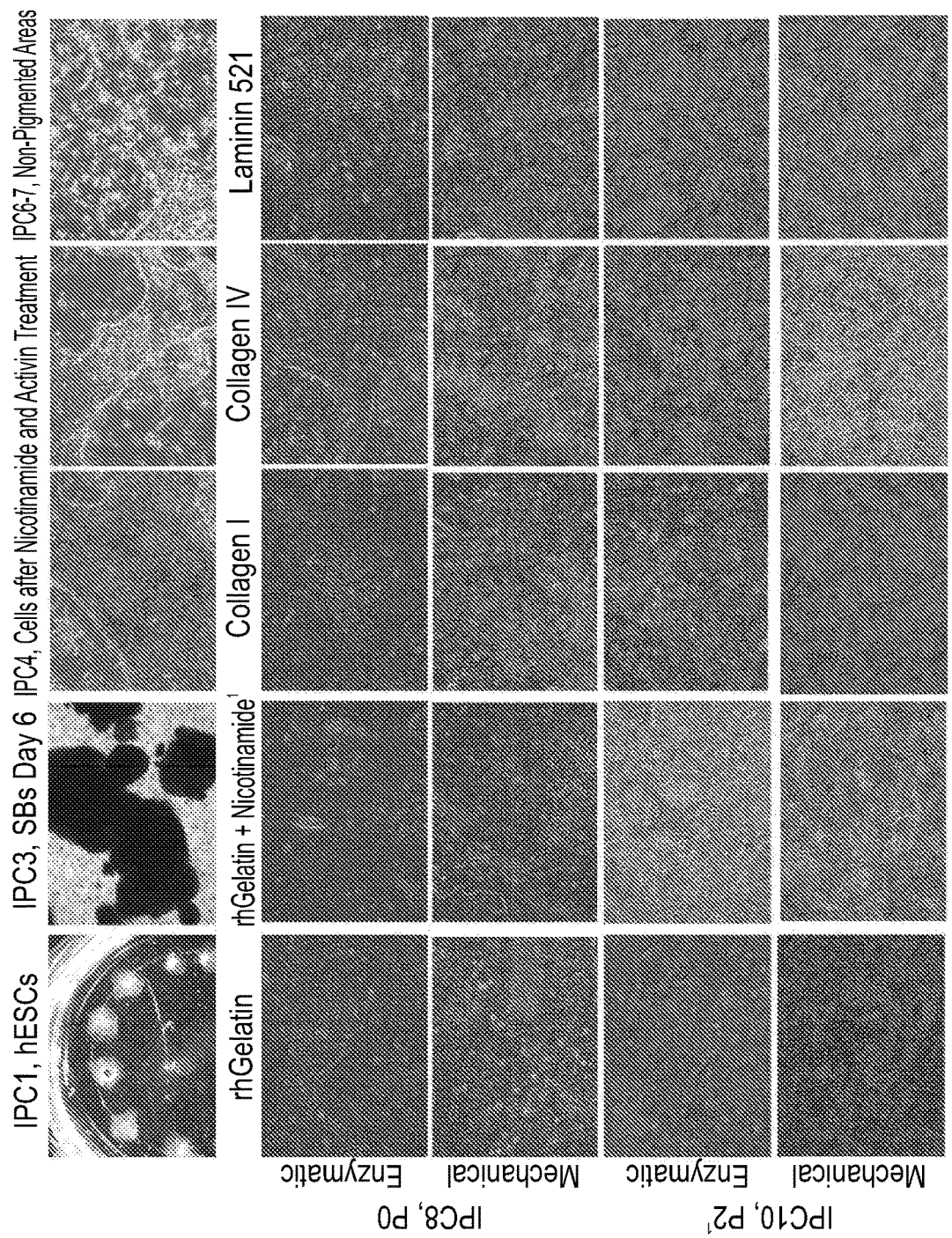
FIG. 4 illustrates the morphology of the RPE cells along the production process.

Tight junctions generated between RPE cells enable the generation of the blood-retinal barrier and a polarized PEDF and VEGF secretion. PEDF is secreted to the apical side where it acts as an anti angiogenic and neurotropic growth factor. VEGF is mainly secreted to the basal side, where it acts as a proangiogenic growth factor on the choroidal endothelium. RPE polarization (barrier function and polarized PEDF and VEGF secretion) was measured in a transwell system at the end of P0 (IPC point 8) in cells that at the end of the production process were isolated mechanically or collected enzymatically and expanded on laminin 521. As can be seen in Table 3, barrier function/trans-epithelial electrical resistance (TEER) was demonstrated as well as polarized secretion of PEDF and VEGF.

ment of the cell culture wells (IPC point 5), the relative area of polygonal/pigmented cells in each well was estimated. 45%±9% (average±SD, n=3 wells of a 6 well plate) of the area was covered with pigmented/polygonal cells (see representative images in FIG. 4). As indicated earlier, areas of pigmented/polygonal cells were negatively selected after manual excision of non-pigmented/non-polygonal areas/cells from some of the cell culture wells and enzymatically collected from the other cell culture wells. Cells collected mechanically and enzymatically were expanded on different matrixes [rhGelatin with and without (control) nicotinamide, Laminin 521, collagen I and collagen IV] and analyzed for morphology at the end of P0 (IPC point 8), P1 (IPC point 9) and P2 (IPC point 10). Morphology at the end of the P0

TABLE 3

Polarization results along the production process

Polarization Lm521

| IPC Point Sampling Time and Stage | | | Mechanical Isolation | | | | Enzymatic Isolation | | | |
|---|---|---|---|---|---|---|---|---|---|---|
| IPC | Week | Stage | PEDF Day 14 (ng/mL/day) | Transwell-TEER (Ω) at Week 3 | Transwell-PEDF ratio at Week 3 (Apical/Basal) | Transwell-VEGF ratio at Week 3 (Basal/Apical) | PEDF Day 14 (ng/mL/day) | Transwell-TEER (Ω) at Week 3 | Transwell-PEDF ratio at Week 3 (Apical/Basal) | Transwell-VEGF ratio at Week 3 (Basal/Apical) |
| 8 | 12 | Passage P0 | 1,737 | 294 | 2.76 | 1.54 | 2,073 | 325 | 2.13 | 2.25 |

Morphology Assessment Along the Production Process:

Cells were analyzed for morphology at various points along the production process (FIG. 4). At the end of the differentiation phase prior to mechanical or enzymatic treatexpansion phase demonstrated a densely packed culture with a typical polygonal-shaped epithelial monolayer morphology in the cell cultures that were originated from mechanically selected pigmented/polygonal cells and grown on the various matrixes. In the cell cultures that were originated from enzymatically collected cells most areas demonstrated this typical morphology while other areas contained cells with different morphology. At the end of P1 and P2 cultures originating from mechanically and enzymatically treated cells demonstrated a similar consistent morphology of densely packed polygonal-shaped epithelial monolayer (FIG. 4).

Viability and Vitality Post Cryopreservation:

At the end of the production process cells collected from mechanical and enzymatic treatments that were expanded on various matrixes [rhGelatin with and without (control) nicotinamide, collagen I, collagen IV and Laminin 521] for 3 passages were harvested and cryopreserved in various xeno/animal free GMP grade cryopreservation media, described in Table 4, at $1.5 \times 10^6$ and $10 \times 10^6$ cells/ml/vial.

TABLE 4A

Cryopreservation of Cells at the End of the Production Process

| Cryo-Medium | Vendor/Cat # | Xeno/Animal Free | Serum Free (Yes/No) | DMSO Free (Yes/No; %) |
|---|---|---|---|---|
| 90% HS/10% DMSO (Control) | Prepared in House | Xeno Free | No | No; 10% |
| CryoStor 5% | BioLife Solutions/CS5 | Animal Free | Yes | No; 5% |
| Stem Cell Banker | AMSBIO/11897 | Animal Free | Yes | No; 5-10% |
| Prime XV ® FreezIS | Irvine Scientific/91140 | Animal Free | Yes | Yes |
| Biological Industries 1 | Material under development | Animal Free | Yes | Yes |
| Biological Industries 2 | Material under development | Animal Free | Yes | Yes |
| Biological Industries 3 | Material under development | Animal Free | Yes | No; 5% |

Viability post thawing (IPC point 11) and vitality of thawed cells one day post seeding were assessed by cell counting (using the Trypan Blue exclusion assay or the Chemometec NC-200 cell counter) and Tox8 (Sigma R-6892). Briefly, drug product cells post thawing were seeded on 96-well plate, in triplicates, at a density of $0.2 \times 10^6$ viable cells/well in a final volume of 0.2 mL DMEM containing 20% human serum per well, for 24 hours at 37° C. and 5% $CO_2$. At the end of the incubation period, culture was assessed by Tox8 (Sigma R-6892) according to manufacturer's instructions) and then cells were washed with PBS, and following TrypLE Select treatment, enumerated using the NC-200 cell counter. Percent vitality was then calculated by dividing the average number of viable adhered cells with the total number of seeded cells per well and multiplying it by 100.

Figure 5A:
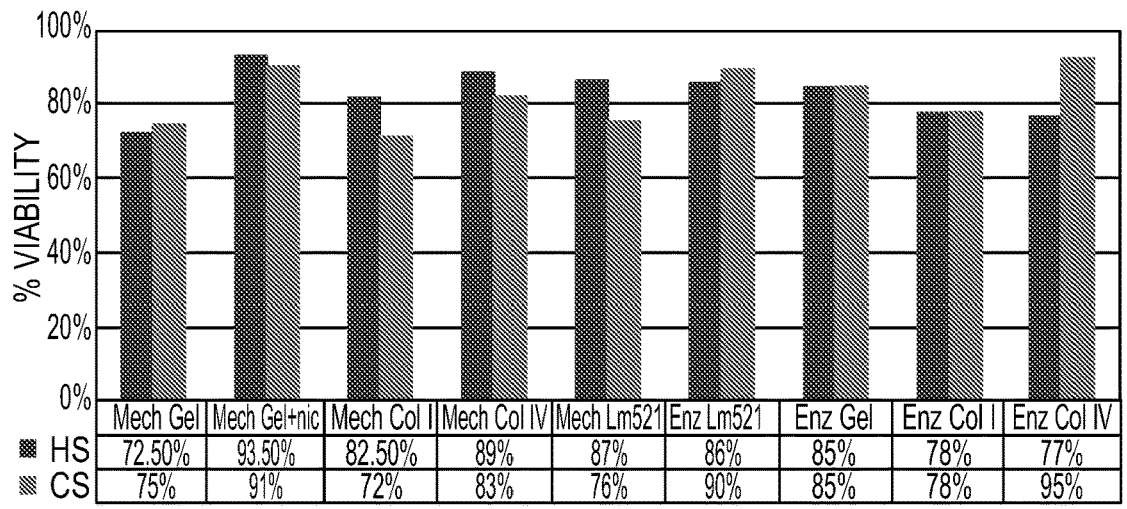
FIGS. 5A-C illustrate that viability and vitality post thawing of mechanically (Mech) isolated and enzymatically (Enz) collected cells that were expanded on various matrixes and cryopreserved in 90% Human Serum (HS) containing 10% DMSO (control; blue bars) or in CryoStor 5% (CS; red bars). Gel, rhGelatin w/ or w/o nicotinamide (Nic); Col I, collagen I; Col IV, collagen IV; Lm521, Laminin 521.
Figure 5B:
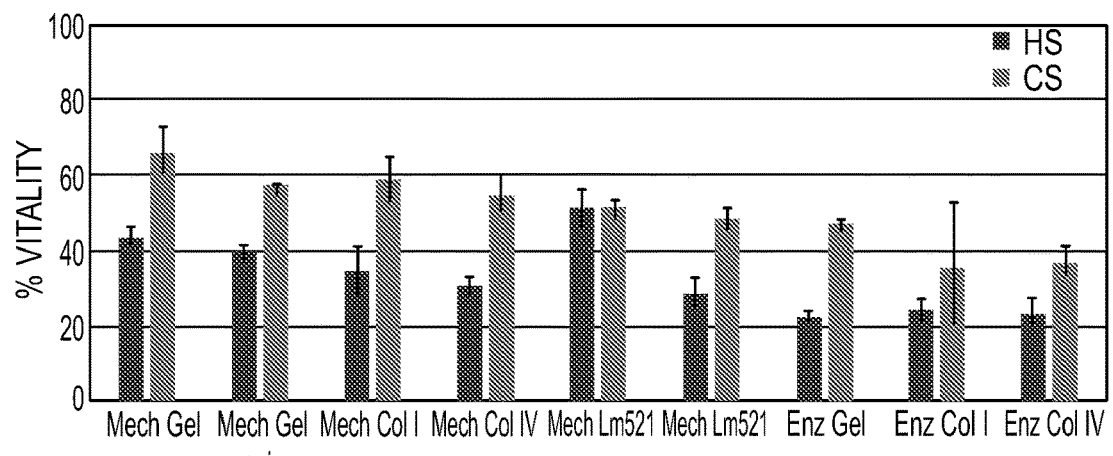
Figure 5C:
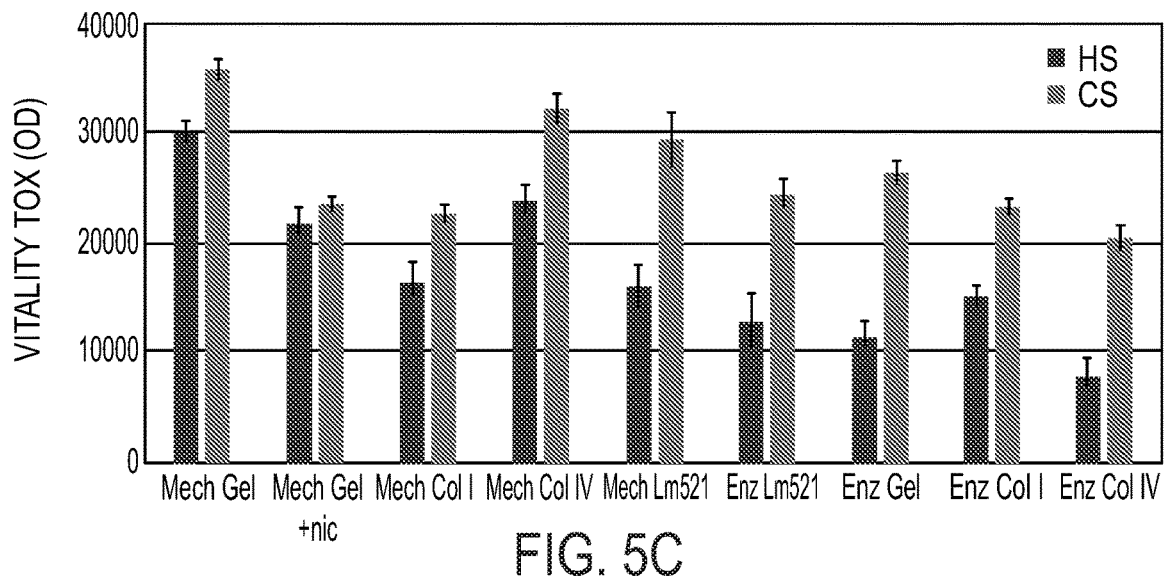

Viability post thawing was similar for cells isolated mechanically and cells collected enzymatically that were expanded on the various matrixes [rhGelatin with and without (control) nicotinamide, collagen I, collagen IV and Laminin 521] and cryopreserved in 90% Human Serum containing 10% DMSO (control; FIG. 5A, blue bars) or in CryoStor 5% (CS; FIG. 5A, red bars), albeit slightly better viability post thawing of cells expanded on rhGelatin with nicotinamide. Although viability post thawing was similar across treatment groups, vitality was significantly better when cells were cryopreserved in CryoStor 5% (FIGS. 5B and 5C, red bars) as compared to cells cryopreserved in 90% Human Serum containing 10% DMSO (FIGS. 5B and 5C, blue bars).

Figure 6B:
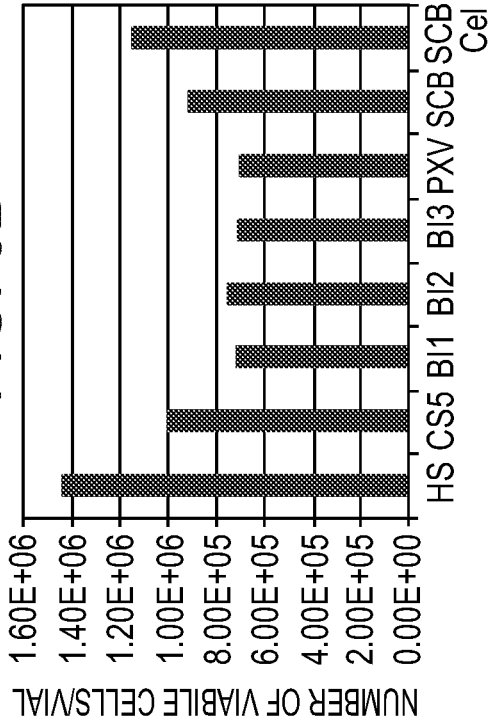
FIGS. 6A-D illustrate viability, total viable cells/vial and vitality post thawing of mechanically isolated cells that were expanded on rhGelatin with nicotinamide and cryopreserved in various cryopreservation media: 90% Human Serum (HS) containing 10% DMSO, CryoStor 5% (CS5), Biological Industries Solutions 1-3 (BI1-3), Prime XV (PXV), Stem Cell Banker (SCB). As a control, viability, total viable cells/vial and vitality post thawing were measured for cells that were expanded on rhGelatin w/o nicotinamide and cryopreserved in SCB (SCB Gel).
Figure 6A:
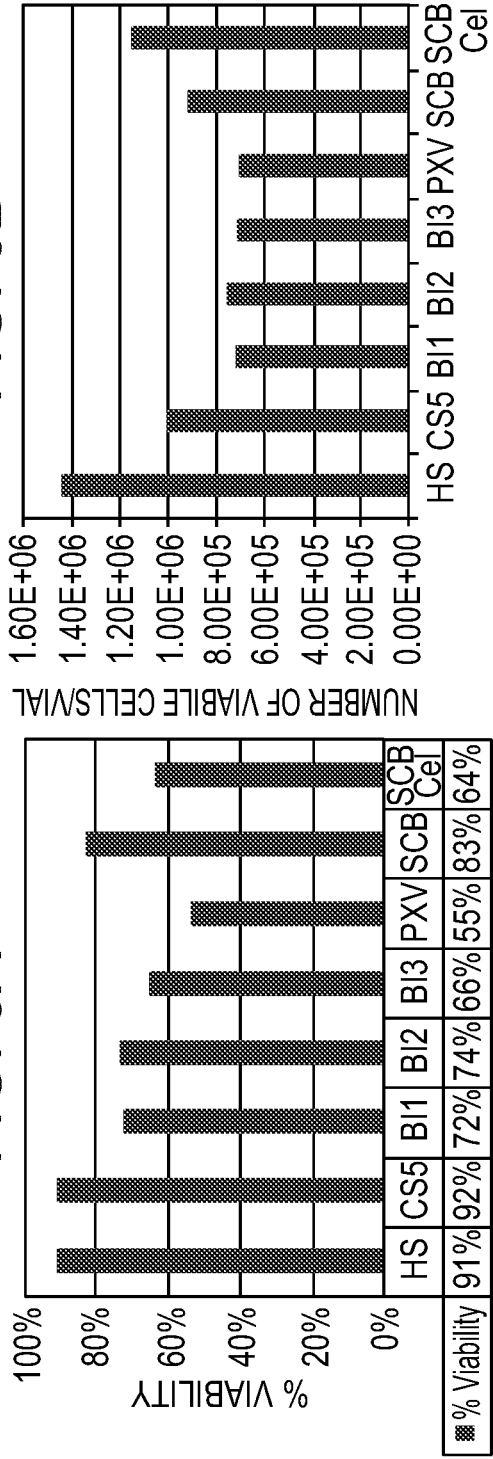
Figure 6D:
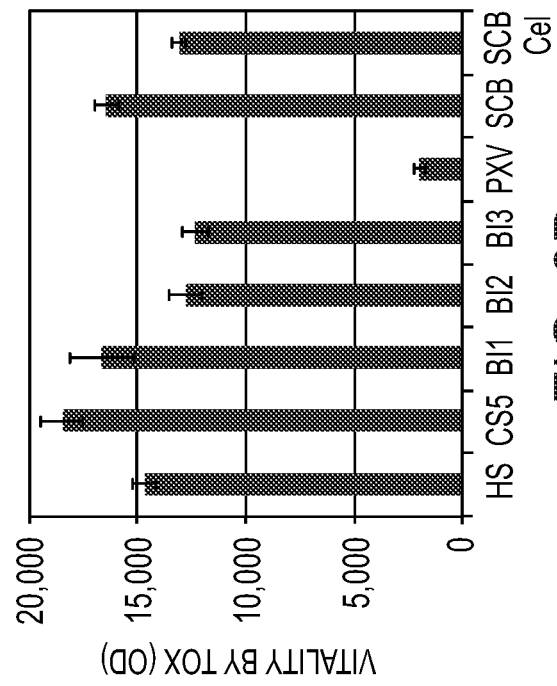
Figure 6C:
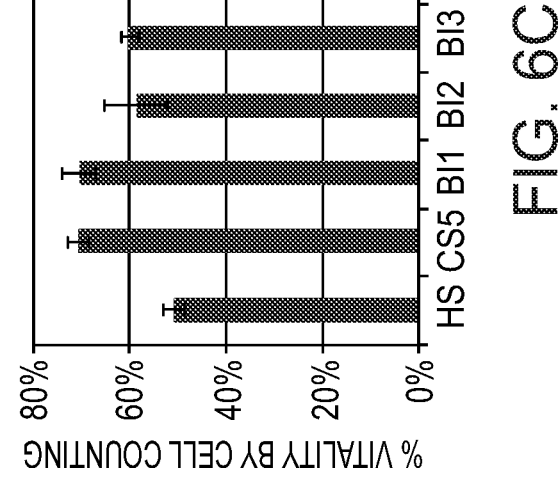

Assessment of post thawing cell viability and vitality of mechanically isolated cells that were expanded on rhGelatin with nicotinamide and cryopreserved in the various freezing media (90% Human Serum containing 10% DMSO, CryoStor 5%, Biological Industries Solutions 1-3, Prime XV and Stem Cell Banker) showed that CryoStor 5% has a significant advantage over the other cryo-media with viability post thawing and vitality after 24 hours in culture of 92% and 70.7%, respectively (FIGS. 6A and 6C, respectively). Viability and vitality of mechanically isolated cells that were expanded on rhGelatin with nicotinamide and cryopreserved in SCB was 83% and 67%, respectively.

Figure 7A:
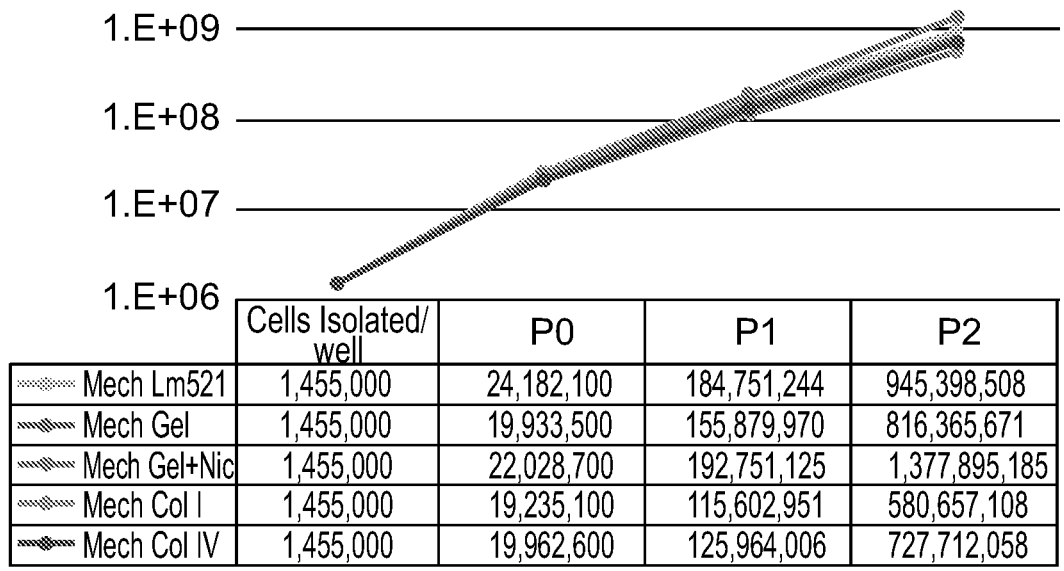
FIGS. 7A-B: Accumulated Cell Yield at the End of the Expansion Phase. Accumulated cell yields following mechanical isolation (A) and enzymatic collection (B).
Figure 7B:
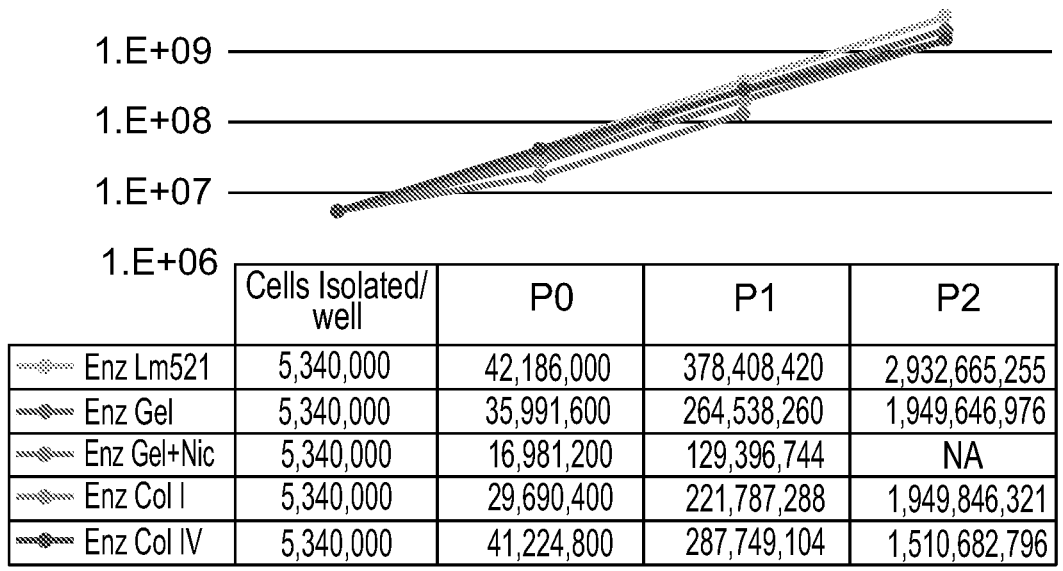

Cell Yield at the End of Production:

At the end of the differentiation phase cells isolated mechanically and cells collected enzymatically were counted and similar numbers of viable cells were seeded per well for 3 expansion cycles on various matrixes [rhGelatin with and without (control) nicotinamide, collagen I, collagen IV and Laminin 521]. At the end of each passage the number of cells per well was measured as well as the accumulated number of cells assuming all cells harvested at each step were seeded. As shown in FIG. 7A, when cells were isolated mechanically, the highest yield was achieved when the cells were expanded on rhGelatin with nicotinamide. When the cells were isolated enzymatically, the highest yield was achieved when the cells were expanded on laminin 521 (FIG. 7B).

Example 2

This Example analyzes the effect of no-mechanical selection of RPE cells generated as in Example 1, in a repeat production process.

Materials and Methods

Figure 1B:
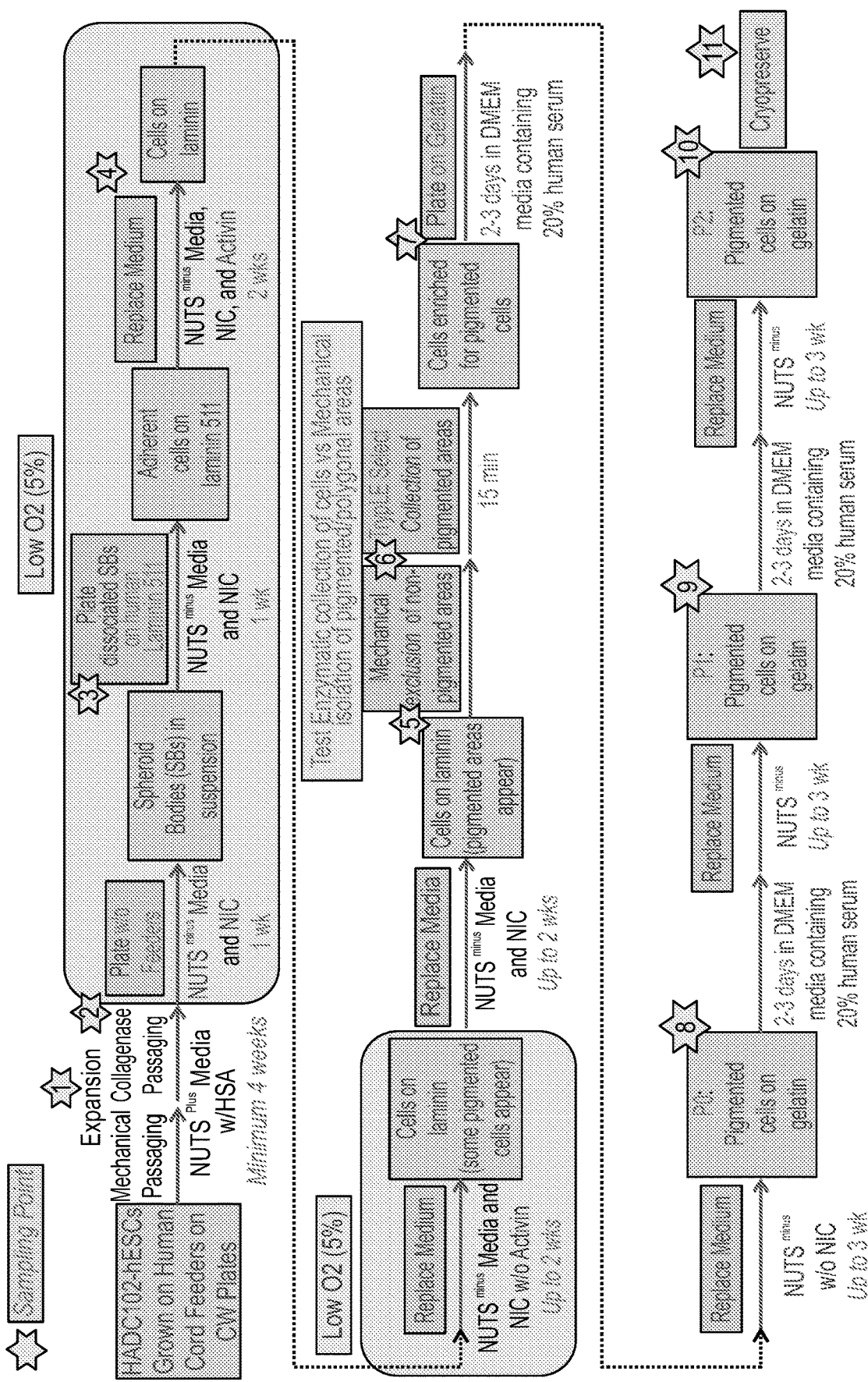
FIG. 1B is an outline of the RPE manufacturing process and in-process control points for Example 2 (yellow stars, In Process Controls, IPCs 1-11). NUTS$^{Plus}$, Nutristem medium containing bFGF and TGFβ; NUTS$^{Minus}$, Nutristem medium w/o bFGF and TGFβ; NIC, Nicotinamide; SBs, Spheroid bodies.

Generation of RPE cells:

xeno-free GMP grade HAD-C 102 hESCs were expanded as colonies on irradiated xeno-free GMP-grade CRD008 hUCFs that were seeded on recombinant human gelatin. hESC expansion was carried out in the presence of Nutristem medium that contains human serum albumin in addition to the growth factors basic FGF and TGF beta (Biological Industries 05-100-1A). Expanded hESCs were then transferred to a suspension culture to initiate differentiation in a directed manner under low $O_2$ conditions (5%). Spheroid bodies (SBs) were formed and then plated as an adherent cell culture under continued directed differentiation conditions towards a neural fate and subsequently towards an RPE cell fate (FIG. 1B). At the end of the differentiation phase, cells were harvested using the following two techniques and expanded 1) Non-pigmented areas were manually excised and removed and the remained pigmented cell areas were enzymatically collected and 2) All cells (pigmented and non-pigmented) were collected enzymatically. Cells were then seeded and expanded for 3 passages on top of rhGelatin covered cell culture plates according to manufacturing instructions. Cells were harvested and cryopreserved at passage 2 (P2) in cryo-medium composed of 90% human serum and 10% DMSO, and in various serum free xeno-free GMP grade cryo-media (CryoStor with 5% DMSO (CS5) and 2% DMSO (CS2), BioLife Solutions).

In some experiments the expansion phase was extended to as many as 11 passages.

FACS Assessment of % Cells Co-Expressing CRALBP and PMEL17:

Cells at various in process control points along the production process were assessed for co-expression of CRALBP and PMEL17. Cells were stained with the Fixable Viability Stain FVS450 (BD, Cat #562247), fixed with 80% Methanol, and co-immunostained with primary mouse anti CRALBP (Clone B2, Abcam Cat #ab15051), or its isotype control (mouse IgG2a; Abcam Cat #ab170191) and rabbit monoclonal anti human PMEL17 (Clone EPR4864, Abcam Cat #ab137062) or its isotype control (rabbit IgG monoclonal; Abcam Cat #ab172730) followed by the secondary antibodies goat anti mouse (Dako Cat #F0479) and goat anti rabbit (Jackson Cat #111-606-144), respectively. Acquisition of FACS data was performed using the Navios flow cytometer (Beckman Coulter) and analysis was performed using the FCS Express 4 software.

FACS Assessment of % Cells Expressing PAX6:

Cells at various in process control points along the production process were assessed for expression of PAX6. Cells were stained with the Fixable Viability Stain FVS450 (BD, Cat #562247), fixed using the Fixation buffer (BD Cat #554655) and permeabilized using Perm buffer III (BD, Cat #558050) and immunostained with mouse anti human PAX6 (BD, Cat #562249). Acquisition of FACS data was performed using the Navios flow cytometer (Beckman Coulter) and analysis was performed using the FCS Express 4 software.

FACS Assessment of % Cells Co-Expressing Oct4 and TRA-1-60:

Cells at various in process control points along the production process were assessed for co-expression of Oct4 and TRA-1-60. Cells were stained with the Fixable Viability Stain FVS450 (BD, Cat #562247), fixed and permeabilized using the Fix/Perm transcription factor buffer set (BD, Cat #562574) and immunostained with mouse anti human Oct3/4 (BD, Cat #562252) and mouse anti human TRA-1-60 (BD, Cat #560193). Acquisition of FACS data was performed using the Navios flow cytometer (Beckman Coulter) and analysis was performed using the FCS Express 4 software. The assay limit of detection is 0.004% and limit of qualification 0.001%.

Immunostaining of Bestrophin 1, MITF and ZO-1: OpRegen drug product cells were thawed, cultured for 24-30 days and then fixed (4% PFA) and permeabilized (using 0.2% Triton X-100 in PBS containing 5% normal donkey serum). The cells were co-immunostained with mouse anti-human Bestrophin 1 (Novus Biologicals, Cat #NB300-164) and rabbit anti-human ZO-1 (Invitrogen, Cat #61-7300) as well as with mouse anti-human MITF (Thermo Fisher Scientific/Neomarkers, Cat #MS772-P1) and rabbit anti-human ZO-1. Cells were washed and immunostained with the secondary antibodies donkey anti rabbit IgG (Jackson, Cat #711-546-152) and donkey anti mouse IgG (Jackson, Cat #715-606-151). Cells were washed and mounted using Vectashield DAPI (Vector Laboratories, Cat #H-1200) and fluorescence mounting medium (DAKO, Cat #S3023). DAPI was added as a counter nuclear stain for the measurement of total cell number. 10× software guided confocal image (Olympus IX82 controlled by FluoView software) was taken from the center of each immunostained cell culture well and a minimum of 500 DAPI positive cells from each image were analyzed for expression of Bestrophin 1 and MITF. Percent Bestrophin 1 and MITF positive cells were calculated.

ELISA Measurement of the Level of Secreted Proteins

Cell culture medium was collected at various in process control points along the production process. Assessment of the level of secreted proteins was performed according to manufacturer's instruction using the ELISA kits noted in Table 4B herein below.

TABLE 4B

| Protein | Kit Name | Vendor | Catalog Number |
|---|---|---|---|
| PEDF | ELISAquant ™ PEDF Sandwich ELISA Antigen Detection Kit | BioProductsMD | PED613 |
| Sgp130 | Human Soluble gp130 Quantikine ELISA Kit | R&D Systems | DGP00 |
| sTNF-R1 | Human sTNF RI/TNFRSF1A Quantikine ELISA Kit | R&D Systems | DRT100 |
| MIF | Human MIF ELISA | RayBiotech | ELH-MIF |
| TRAIL-R3 | Human TRAIL R3 ELISA | RayBiotech | ELH-TRAILR3 |
| IL-6 | Human IL-6 Quantikine ELISA Kit | R&D Systems | D6050 |
| VEGF | Human VEGF Quantikine ELISA Kit | R&D Systems | SVE00 |
| Angiogenin | Human Angiogenin Quantikine ELISA Kit | R&D Systems | DAN00 |
| TIMP-1 | Human TIMP-1 Quantikine ELISA Kit | R&D Systems | DTM100 |
| TIMP-2 | Human TIMP-2 Quantikine ELISA Kit | R&D Systems | DTM200 |
| Axl | Human Axl ELISA | RayBiotech | ELH-AXL |

Assessment of Glucose Consumption and Lactate Production:

Cell culture medium was collected at various in process control points along the production process. The levels of glucose and lactate were measured using Accutrend Plus (Cobas) meter with pre-calibrated strips for Glucose (Cobas, Cat #11447475) and Lactate (Cobas, Cat #03012654).

Assessment of Barrier Function and Polarized PEDF and VEGF Secretion:

OpRegen drug product was thawed and cultured for 14 days in the presence of nicotinamide. Then cells are transferred to a transwell (Costar 3460, 0.4 μm) for additional 4 weeks during which Trans Epithelial Resistance (TEER; barrier function) was measured and medium was collected from the upper and lower transwell chambers on a weekly basis for assessment of PEDF and VEGF secretion. The ratios of apical to basal PEDF secretion and basal to apical VEGF secretion are reported.

Results

A batch release of the drug product cells generated as described above is presented in Table 5.

TABLE 5

| Test | Acceptance Criteria | Mechanical | Enzymatic |
|---|---|---|---|
| Viability | ≥70% | 86% (n = 2) | 89% (n = 2) |
| Total Cells/Vial | ≥0.8 × 10⁶/vial | 1.17 × 10⁶/vial (n = 2) | 0.88 × 10⁶/vial (n = 2) |
| RPE Identity: | ≥80% | | |
| % MITF Positive Cells | | 94% | 96% |
| % Bestrophin 1 Positive Cells | | 95% | 92% |
| RPE Purity | ≥95% | 99.87% | 99.35% |
| % CRALBP⁺PMEL17⁺ RPE Cells | | | |
| hESC Impurity | <0.01% | 0.000% (BLOD) | 0.000% (BLOD) |
| % Oct4⁺TRA-1-60⁺ hESCs | | | |
| Potency: | | | |
| • Barrier Function (TEER) Week 3 | ≥100 Ω | Interim Data Week 2: 286 Ω | Interim Data Week 2: 352 Ω |

* When TEER is >100 Ω polarized PEDF and VEGF secretion is expected; BLOD: Below Limit of Detection (i.e. below 0.004%)

Figure 12:
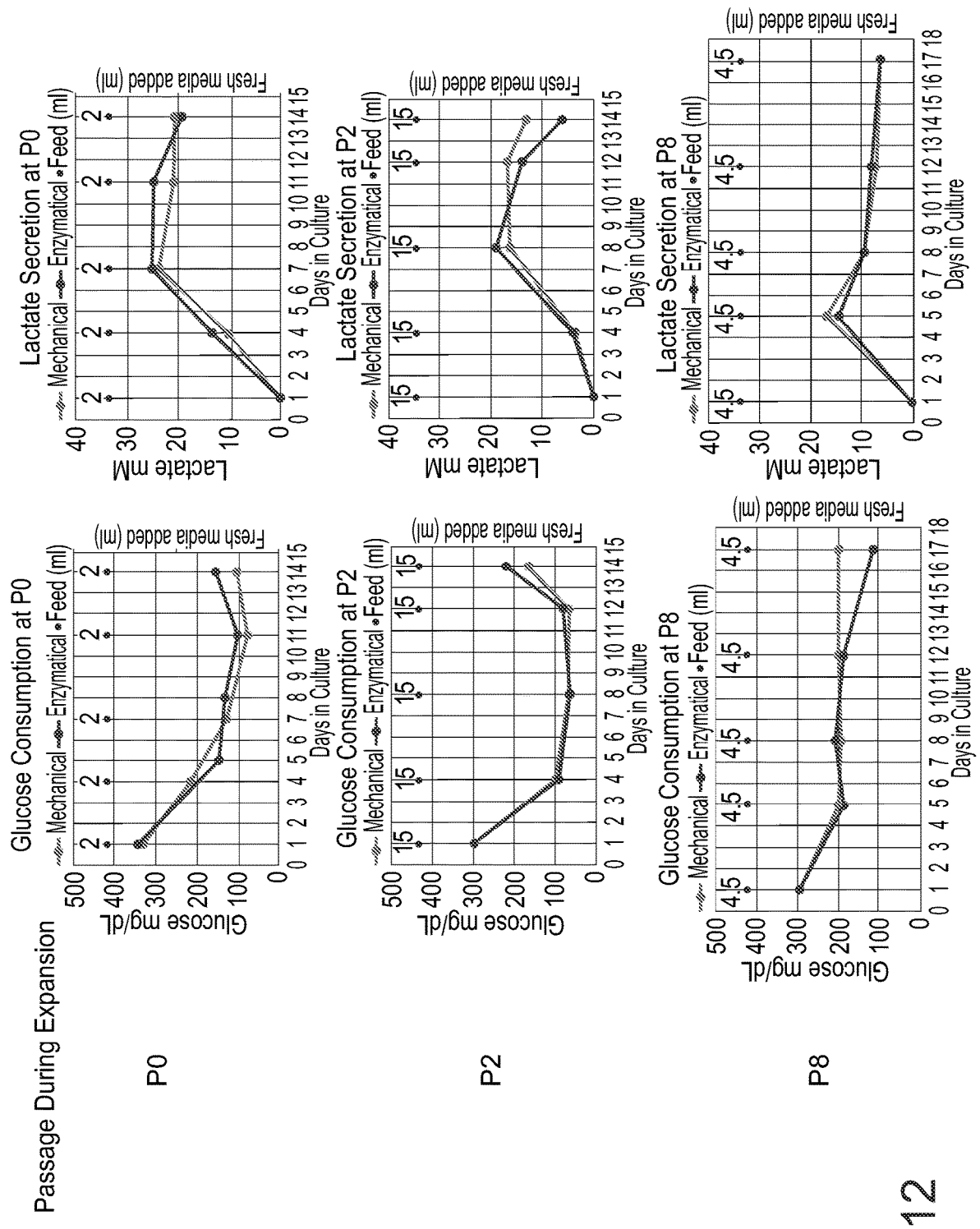
FIG. 12 presents graphs comparing glucose and lactate growth profiles in cells along production process 2 using enzymatic collection of all cells or mechanical isolation of polygonal/pigmented cells at different passages along the RPE expansion phase.

Cells that underwent mechanical isolation demonstrated similar glucose and lactate profiles during their expansion as compared with cells that were collected enzymatically—see FIG. 12.

Figure 8:
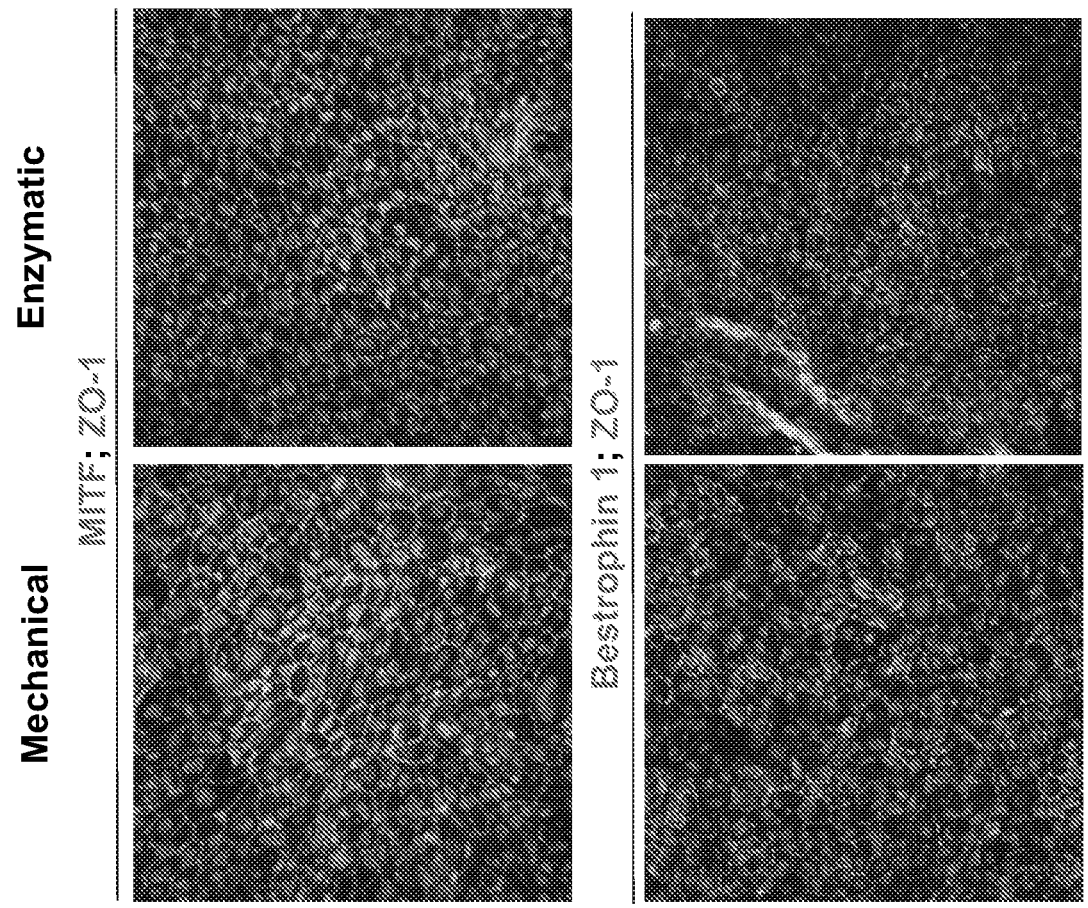
FIG. 8 illustrates co-staining of the drug product RPE cells from process 2 using MITF and Zo-1 and bestrophin-1 and Zo-1 antibodies.

MITF and Bestrophin 1 Staining:

The expression of MITF and bestrophin 1 was analyzed on drug product cells. As can be seen from FIG. 8, RPE cells generated without mechanical isolation expressed MITF and bestrophin 1 to the same extent as RPE cells generated using the identical differentiation process, but with mechanical isolation. The results are quantified in Table 6 herein below.

TABLE 6

| Identity | Mechanical | Enzymatic |
|---|---|---|
| % MITF | 94% | 96% |
| % Bestrophin 1 | 95% | 92% |

CRALBP/PMEL17 RPE Purity Along the Production Process:

Assessment of CRALBP⁺PMEL17⁺ cells for measurement of RPE purity was performed at the end of the differentiation phase following enzymatic collection of all cells and mechanical isolation of polygonal/pigmented cells (In Process Controls, IPCs, 5-7), at P0 (IPC 8) and at P2 post cryopreservation (Drug Product, IPC 11).

The results are illustrated in FIG. 9 and summarized in Table 7 herein below.

TABLE 7

% CRALBP + PMEL17 + RPE Cells Along OpRegen Production Process (Mock 7)

| IPC | Stage | Mechanical | Enzymatic |
|---|---|---|---|
| 5 | End of Differentiation | NA | 17.58 |
| 6 | | 0.32 | NA |
| 7 | | 36.62 | NA |
| 8 | Expansion P0 | 86.15 | 49.96 |
| 9 | Expansion P1 | 99.70 | 85.87 |
| 10 | Expansion P2, Drug Substance | ND | 99.11 |
| 11 | P2, Drug Product | 99.87 | 99.35 |

Measurement of Non-Differentiated hESCs Along the Production Process:

FACS analysis was carried out in order to analyze the extent of residual non-differentiated hESCs (Oct4+ TRA-1-60+) in the RPE cells.

Figure 10:
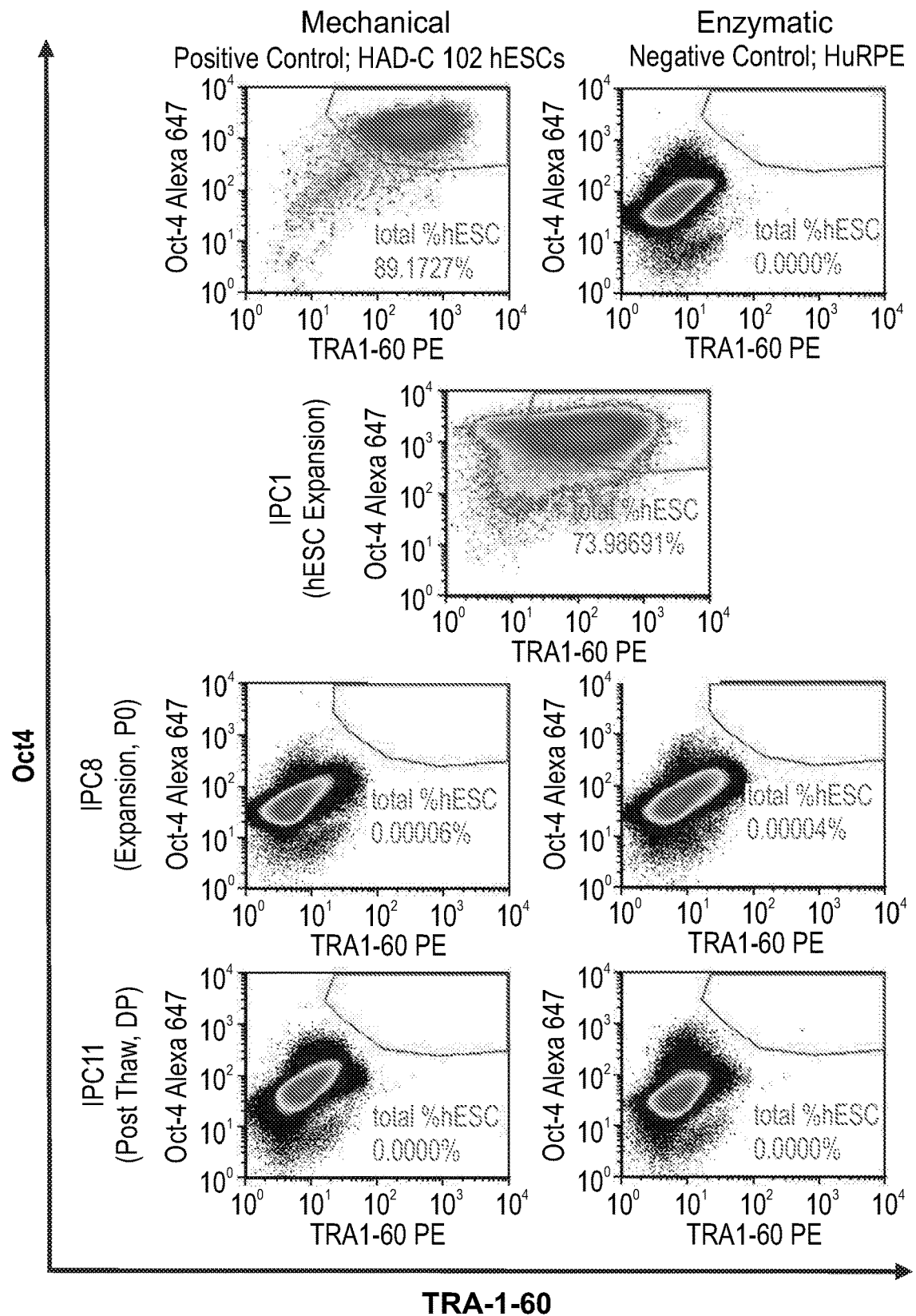
FIG. 10 illustrates % Oct4+Tra-1-60+ cells along production process 2. Density plots of IPC points 1, 8 and 11, and representative density plots of positive control RPE and negative control hESCs are presented. Numbers indicate percent Oct4+TRA-1-60+ double positive cells out of the live single cell gated population.

The results are summarized in Table 8 and presented in FIG. 10.

TABLE 8

% Oct4 + TRA-1-60 + hESCs Along OpRegen Production Process (Mock 7)

| IPC | Stage | Mechanical | Enzymatic |
|---|---|---|---|
| 1 | Mechanically expanded hESCs | 73.98% | |
| 8 | Expansion P0 | 0.00006% (BLOD) | 0.00004% (BLOD) |
| 11 | P2, Drug Product | 0.0000 (BLOD) | 0.0000 (BLOD) |

BLOD: Below Limit of Detection (i.e. below 0.004%)

Factor Secretion along the Production Process: PEDF, TIMP-2, sgp130 and sTNF-R1 secretion was measured along the production process. The results are illustrated in Table 9, herein below.

TABLE 9

| | | PEDF (ng/mL/day) | | TIMP-2 (ng/mL/day) | | sgp130 (ng/mL/day) | | sTNF-R1 pg/mL/day | |
|---|---|---|---|---|---|---|---|---|---|
| IPC | Stage | Mechanical | Enzymatic | Mechanical | Enzymatic | Mechanical | Enzymatic | Mechanical | Enzymatic |
| 1 | Mechanically expanded hESCs | 6.5 | | 18 | | 0.64 | | 120 | |
| 2 | Collagenase Passaged hESCs | 4.7 | | 3.55 | | 0.20 | | 21 | |
| 3 | Spheroid Bodies | 2 | | 1.80 | | 0.09 | | 33 | |
| 4 | End of Activin A | 101 | | 8.25 | | 0.26 | | 30 | |
| 5 | End of Differentiation | 252 | | 22 | | 0.38 | | 63 | |
| 6 | | NA | NA | NA | NA | NA | NA | NA | NA |
| 7 | | NA | NA | NA | NA | NA | NA | NA | NA |
| 8 | Expansion P0 | 1676 | 737 | 65 | 49 | 0.78 | 0.62 | 194 | 143 |
| 9 | Expansion P1 | 7955.47 | 381 | 67 | 83 | 0.94 | 0.60 | 771 | 166 |
| 10 | Expansion P2, Drug Substance | 17792 | 25034 | 115 | 120 | 2.06 | 2.17 | 611 | 2362 |

VEGF, angiogenin, TIMP-1 and MIF secretion was measured along the production process. The results are illustrated in Table 10, herein below.

well up to expansion cycles on rhGelatin. At the end of each passage the number of cells was measured as well as the accumulated number of cells assuming all cells harvested at

TABLE 10

| IPC | Stage | VEGF (pg/mL/day) | | Angiogenin (pg/mL/day) | | TIMP-1 (ng/mL/day) | | MIF ng/mL/day | |
|---|---|---|---|---|---|---|---|---|---|
| | | Mechanical | Enzymatic | Mechanical | Enzymatic | Mechanical | Enzymatic | Mechanical | Enzymatic |
| 1 | Mechanically expanded hESCs | 0 | | 232 | | ND | | 14 | |
| 2 | Collagenase Passaged hESCs | 0 | | 126 | | 33 | | 100 | |
| 3 | Spheroid Bodies | 0 | | 94 | | 21 | | 30 | |
| 4 | End of Activin A | 230 | | 184 | | 5 | | 57 | |
| 5 | End of | 150 | | 335 | | 7 | | 35 | |
| 6 | Differentiation | NA | NA | NA | NA | NA | NA | NA | NA |
| 7 | | NA | NA | NA | NA | NA | NA | NA | NA |
| 8 | Expansion P0 | 100 | 500 | 746 | 533 | 19 | 22 | 7 | 14 |
| 9 | Expansion P1 | 730 | 700 | 641 | 662 | 23 | 20 | 34 | 9 |
| 10 | Expansion P2, Drug Substance | 350 | 590 | 1231 | 835 | 53 | 51 | 31 | 21 |

VEGF, angiogenin, TIMP-1 and MIF secretion was measured along the production process. The results are illustrated in Table 11, herein below.

TABLE 11

| IPC | Stage | Axl (pg/mL/day) | | IL-6 (ng/mL/day) | | TRAIL-R3 (ng/mL/day) | |
|---|---|---|---|---|---|---|---|
| | | Mechanical | Enzymatic | Mechanical | Enzymatic | Mechanical | Enzymatic |
| 1 | Mechanically expanded hESCs | 320 | | ND | | 34.7 | |
| 2 | Collagenase Passaged hESCs | 119 | | ND | | 41.1 | |
| 3 | Spheroid Bodies | 45 | | ND | | 0 | |
| 4 | End of Activin A | 185 | | 2.1 | | 31.7 | |
| 5 | End of | 249 | | 1.9 | | 0 | |
| 6 | Differentiation | NA | NA | NA | NA | NA | NA |
| 7 | | NA | NA | NA | NA | NA | NA |
| 8 | Expansion P0 | 2505 | 1651 | 14.2 | 3.9 | 55.6 | 227.6 |
| 9 | Expansion P1 | 2656 | 2693 | 33.4 | 6.5 | 97.9 | 85.4 |
| 10 | Expansion P2, Drug Substance | 3866 | 4360 | 60.2 | 53.7 | 154.8 | ND |

Measurement of Pax6+ Cells Along the Production Process:

FACS analysis was carried out in order to analyze the percentage of Pax6+ cells.

The results are summarized in Table 12 and presented in FIG. 11.

TABLE 12

| IPC | Stage | Mechanical | Enzymatic |
|---|---|---|---|
| 8 | Expansion P0 | 99.86% | 94.07% |
| 11 | P2, Drug Product | 98.52% | 96.7% |

Cell Yield at the End of Production:

At the end of the differentiation phase cells isolated mechanically and cells collected enzymatically were counted and similar numbers of viable cells were seeded per each step were seeded. As shown in Table 13, the enzymatically isolated cells demonstrated higher cell yield and higher number of total cell doublings.

TABLE 13

| | Yield (# Cells per End of Differentiation Well) | | Total # Cell Doublings | |
|---|---|---|---|---|
| Stage | Mechanical | Enzymatic | Mechanical | Enzymatic |
| End of differentiation | 2.95E+06 | 2.90E+06 | NA | NA |
| Passage P0 | 3.88E+07 | 2.33E+07 | 3.7 | 3.0 |
| Passage P1 | 1.91E+08 | 1.85E+08 | 7.3 | 7.2 |
| Passage P2 | 6.96E+08 | 1.33E+09 | 9.7 | 10.7 |
| Passage P3 | 2.74E+09 | 6.55E+09 | 12.0 | 13.4 |
| Passage P4 | 1.65E+10 | 4.16E+10 | 15.9 | 17.0 |
| Passage P5 | 6.21E+10 | 2.05E+11 | 17.9 | 19.3 |
| Passage P6 | 7.57E+11 | 2.62E+12 | 22.2 | 23.4 |
| Passage P7 | 9.06E+11 | 2.34E+12 | 24.1 | 24.8 |
| Passage P8 | 5.37E+11 | 5.10E+12 | 26.9 | 26.0 |

TABLE 13-continued

| | Yield (# Cells per End of Differentiation Well) | | Total # Cell Doublings | |
|---|---|---|---|---|
| Stage | Mechanical | Enzymatic | Mechanical | Enzymatic |
| Passage P9 | * | 1.42E+13 | * | 28.8 |
| Passage P10 | * | 3.41E+13 | * | 31.2 |
| Passage P11 | * | 1.15E+13 | * | 33.3 |

* Cells could not be further expanded

These data demonstrates that when all cells are collected enzymatically, the expansion phase can be extended.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of generating retinal pigment epithelial (RPE) cells comprising:
   (a) further differentiating a population of differentiating cells in a culture comprising a medium comprising one or more members of the TGFβ superfamily, thereby generating a mixed population of cells comprising RPE cells;
   (b) enzymatically removing said mixed population of cells from said culture without mechanical isolation of cells, wherein more than 10% of the cells of said mixed populations of cells are non-pigmented cells; and
   (c) expanding said mixed population of cells to generate an expanded population of RPE cells.

2. The method of claim 1, wherein more than 50% of all the cells in said culture are removed in step (b).

3. The method of claim 1, further comprising differentiating a population of human pluripotent stem cells in a medium comprising a differentiating agent selected from small molecules and proteins to generate a population of differentiating cells prior to step (a).

4. The method of claim 3, wherein said differentiating agent comprises nicotinamide.

5. The method of claim 4, wherein said medium prior to step (a) is devoid of activin A.

6. The method of claim 1, wherein said member of the TGFβ superfamily is selected from the group consisting of TGFβ1, TGFβ3, and activin A.

7. The method of claim 3, wherein said medium prior to step (a) comprises nicotinamide and activin A.

8. The method of claim 3, further comprising a step of culturing said RPE cells in a medium comprising nicotinamide and devoid of activin A following step (a) and prior to step (b).

9. The method of claim 3, wherein the differentiating prior to step (a) is carried out under non-adherent conditions.

10. The method of claim 3, wherein the differentiating prior to step (a) is carried out initially under non-adherent conditions and subsequently under adherent conditions.

11. The method of claim 3, wherein differentiating the pluripotent stem cells is carried out for at least 5 days or at least 7 days.

12. The method of claim 3, wherein at least a portion of said differentiating is carried out under conditions wherein the atmospheric oxygen level is less than about 10%.

13. The method of claim 3, wherein said differentiating is carried out under conditions wherein the atmospheric oxygen level is greater than about 10%.

14. The method of claim 1, wherein more than 70% of the cells of said expanded population of RPE cells are CRALBP$^+$PMEL17$^+$.

15. The method of claim 1, wherein the mixed population of cells are expanded on an adherent surface, wherein the adherent surface is selected from the group consisting of gelatin, laminin, fibronectin, collagen I and collagen IV, and wherein the population of cells is expanded on said adherent surface for at least about 3 weeks.

16. The method of claim 1, wherein said population of cells is capable of being expanded for more than about 3 passages, more than about 5 passages, 8 passages, 10 passages or more than about 15 passages.

17. The method of claim 1, wherein said expanded population of RPE cells is capable of undergoing more than 30 cell doublings.

18. The method of claim 3, wherein said human pluripotent stem cells comprise human embryonic stem cells.

19. The method of claim 1, wherein the expanded population of RPE cells comprises at least about $1.15 \times 10^{13}$ cells.

20. The method of claim 1, wherein the trans-epithelial electrical resistance of the expanded population of RPE cells is greater than about 100 ohms.

* * * * *